(12) United States Patent
Krueger et al.

(10) Patent No.: US 8,277,506 B2
(45) Date of Patent: Oct. 2, 2012

(54) METHOD AND STRUCTURE FOR STABILIZING A VERTEBRAL BODY

(75) Inventors: John Krueger, Muskego, WI (US); Evan Linderman, Northbrook, IL (US); Louis Mingione, Chicago, IL (US); Erin Schaus, Elk Grove Village, IL (US); James Kantola, Waukegan, IL (US); Talya Reilly, Chicago, IL (US); Shayna Massi, Chicago, IL (US)

(73) Assignee: CareFusion 2200, Inc., San Diego, CA (US)

( * ) Notice: Subject to any disclaimer, the term of this patent is extended or adjusted under 35 U.S.C. 154(b) by 306 days.

(21) Appl. No.: 12/489,237

(22) Filed: Jun. 22, 2009

(65) Prior Publication Data

US 2010/0100184 A1    Apr. 22, 2010

Related U.S. Application Data

(60) Provisional application No. 61/075,202, filed on Jun. 24, 2008.

(51) Int. Cl.
*A61F 2/44* (2006.01)
(52) U.S. Cl. .......... 623/17.12; 606/279; 606/93
(58) Field of Classification Search .......... 606/279, 606/92–99, 90; 623/17.11–17.16
See application file for complete search history.

(56) References Cited

U.S. PATENT DOCUMENTS

| | | | |
|---|---|---|---|
| 4,265,231 A | 5/1981 | Scheller, Jr. et al. | |
| 5,295,980 A | 3/1994 | Ersek | |
| 5,609,629 A | 3/1997 | Fearnot et al. | |
| 5,732,698 A | 3/1998 | Swanson et al. | |
| 5,843,103 A | 12/1998 | Wulfman | |
| 5,851,209 A | 12/1998 | Kummer et al. | |
| 5,879,353 A | 3/1999 | Terry | |
| 5,891,147 A | 4/1999 | Moskovitz et al. | |
| 5,928,239 A | 7/1999 | Mirza | |
| 5,972,015 A | 10/1999 | Scribner et al. | |
| 6,048,346 A | 4/2000 | Reiley et al. | |
| 6,066,154 A | 5/2000 | Reiley et al. | |
| 6,171,312 B1 * | 1/2001 | Beaty | 606/80 |

(Continued)

FOREIGN PATENT DOCUMENTS

EP      1459691 A1     9/2004
(Continued)

OTHER PUBLICATIONS

International Search Report for International Application No. PCT/US2009/048212, dated Oct. 12, 2009, 3 pages.

(Continued)

*Primary Examiner* — Eduardo C Robert
*Assistant Examiner* — James Palmer
(74) *Attorney, Agent, or Firm* — Brinks Hofer Gilson & Lione

(57) ABSTRACT

An apparatus for stabilizing a vertebral body using a structural support to stabilize the vertebral body. The apparatus includes a first curable material deposit proximal to a first endplate of a vertebral body for providing support to the first endplate of the vertebral body and a second curable material deposit proximal to a second endplate of a vertebral body for providing support to a second endplate of the vertebral body. The apparatus also utilizes a stabilizing structure between the first curable material deposit and the second curable material deposit and connecting the first curable material deposit and the second curable material deposit for providing support to the vertebral body.

10 Claims, 24 Drawing Sheets

U.S. PATENT DOCUMENTS

| | | | |
|---|---|---|---|
| 6,241,734 B1 | 6/2001 | Scribner et al. | |
| 6,248,110 B1 | 6/2001 | Reiley et al. | |
| 6,296,639 B1 | 10/2001 | Truckai et al. | |
| 6,328,744 B1 | 12/2001 | Harari et al. | |
| 6,358,251 B1 | 3/2002 | Mirza | |
| 6,383,188 B2 | 5/2002 | Kuslich et al. | |
| 6,383,190 B1 | 5/2002 | Preissman | |
| 6,425,887 B1 | 7/2002 | McGuckin et al. | |
| 6,440,138 B1 | 8/2002 | Reiley et al. | |
| 6,494,868 B2 | 12/2002 | Amar | |
| 6,575,978 B2 | 6/2003 | Peterson et al. | |
| 6,592,559 B1 | 7/2003 | Pakter et al. | |
| 6,641,587 B2 | 11/2003 | Scribner et al. | |
| 6,645,213 B2 | 11/2003 | Sand et al. | |
| 6,676,664 B1 | 1/2004 | Al Assir | |
| 6,679,886 B2 | 1/2004 | Weikel et al. | |
| 6,740,090 B1 | 5/2004 | Cragg et al. | |
| 6,746,451 B2 | 6/2004 | Middleton et al. | |
| 6,783,515 B1 | 8/2004 | Miller et al. | |
| 6,790,210 B1 | 9/2004 | Cragg et al. | |
| 6,793,660 B2 | 9/2004 | Kerr et al. | |
| 6,814,734 B2 | 11/2004 | Chappuis et al. | |
| 6,843,796 B2 | 1/2005 | Harari et al. | |
| 6,863,672 B2 | 3/2005 | Reiley et al. | |
| 6,875,219 B2 | 4/2005 | Arramon et al. | |
| 6,921,403 B2 | 7/2005 | Cragg et al. | |
| 6,923,813 B2 | 8/2005 | Phillips et al. | |
| 7,004,945 B2 | 2/2006 | Boyd et al. | |
| 7,025,771 B2 | 4/2006 | Kuslich et al. | |
| 7,048,743 B2 | 5/2006 | Miller et al. | |
| 7,066,942 B2 | 6/2006 | Treace | |
| 7,087,040 B2 | 8/2006 | McGuckin, Jr. et al. | |
| 7,087,058 B2 | 8/2006 | Cragg | |
| 7,114,501 B2 | 10/2006 | Johnson et al. | |
| 7,226,481 B2 * | 6/2007 | Kuslich | 623/17.11 |
| 2002/0099384 A1 | 7/2002 | Scribner et al. | |
| 2002/0120240 A1 | 8/2002 | Bagga et al. | |
| 2002/0156483 A1 | 10/2002 | Voellmicke et al. | |
| 2003/0036762 A1 | 2/2003 | Kerr et al. | |
| 2003/0078589 A1 | 4/2003 | Preissman | |
| 2004/0068264 A1 | 4/2004 | Treace | |
| 2004/0068267 A1 | 4/2004 | Harvie et al. | |
| 2004/0162559 A1 | 8/2004 | Arramon et al. | |
| 2004/0215202 A1 | 10/2004 | Preissman | |
| 2005/0038432 A1 | 2/2005 | Shaolian et al. | |
| 2005/0070913 A1 | 3/2005 | Milbocker et al. | |
| 2005/0182414 A1 * | 8/2005 | Manzi et al. | 606/86 |
| 2006/0009779 A1 | 1/2006 | Collins et al. | |
| 2006/0064101 A1 | 3/2006 | Arramon | |
| 2006/0116643 A1 | 6/2006 | Dixon | |
| 2006/0149280 A1 | 7/2006 | Harvie et al. | |
| 2006/0173464 A1 * | 8/2006 | Ellman et al. | 606/93 |
| 2006/0195094 A1 | 8/2006 | McGraw et al. | |
| 2006/0217736 A1 | 9/2006 | Kaneko et al. | |
| 2006/0241624 A1 | 10/2006 | Kizuka et al. | |
| 2006/0264967 A1 | 11/2006 | Ferreyro et al. | |
| 2007/0142842 A1 * | 6/2007 | Krueger et al. | 606/92 |
| 2007/0233258 A1 | 10/2007 | Hestad et al. | |
| 2010/0152855 A1 * | 6/2010 | Kuslich et al. | 623/17.12 |

FOREIGN PATENT DOCUMENTS

WO    WO 98/56301 A1    12/1998

OTHER PUBLICATIONS

Specification of U.S. Appl. No. 12/633,358, filed Dec. 8, 2009.
Specification of U.S. Appl. No. 12/634,366, filed Dec. 9, 2009.

* cited by examiner

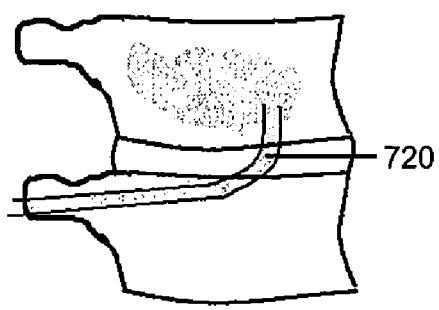 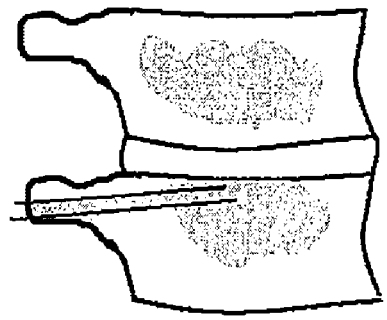
Fig. 34A       Fig. 34B
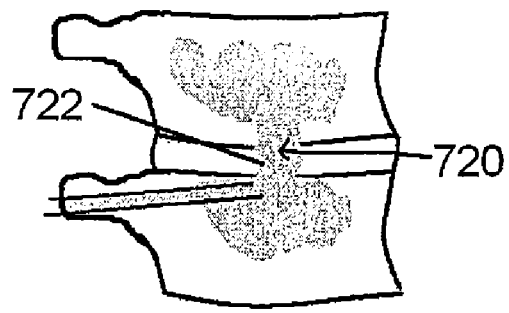
Fig. 34C
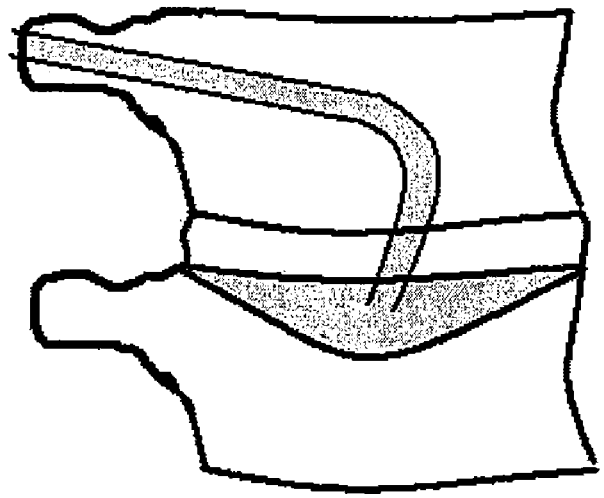
Fig. 35

METHOD AND STRUCTURE FOR STABILIZING A VERTEBRAL BODY

CLAIM OF PRIORITY

This application claims the benefit, pursuant to 35 USC 119(e), of the earlier filing date of U.S. Provisional Patent Application Ser. No. 61/075,202, entitled "METHOD AND STRUCTURE FOR STABILIZING A VERTEBRAL BODY," filed in the US Patent Office on Jun. 24, 2008, the contents of which are incorporated by reference, herein.

BACKGROUND

The present invention relates to devices and methods for stabilizing vertebral bodies. More particularly, it relates to devices, systems and methods for stabilizing vertebral bodies with curable material or other stabilizing structures.

Surgical intervention at damaged or compromised bone sites has proven highly beneficial for patients, for example patients with back pain associated with vertebral damage. During certain bone procedures, cancellous bone within a vertebral body is supplemented by an injection of a palliative (or curative) material employed to stabilize the trabeculae. For example, superior and inferior vertebrae in the spine can be beneficially stabilized by the injection of an appropriate, curable material (e.g., PMMA or other bone cement). In other procedures, percutaneous injection of stabilization material into vertebral compression fractures by, for example, transpedicular or parapedicular approaches, has proven beneficial in relieving pain and stabilizing damaged bone sites. Other skeletal bones (e.g., the femur) can be treated in a similar fashion. In any regard, bone in general, and cancellous bone in particular, can be strengthened and stabilized by a palliative injection of bone-compatible material.

The conventional technique for stabilizing a damaged vertebral body includes accessing the interior of the vertebral body according to known techniques and delivering curable material to the interior of the vertebral body in a cloud-like formation. The convention technique presents several shortcomings. The cloud-like formation creates a somewhat spherical hardened structure within the vertebral body that provides gradations of support to the endplates of the vertebral body. The cloud-like formation may only provide support at a point or a relatively small portion of an endplate. Because the cloud-like formation does not distribute force broadly over the surface of an endplate, pressure points within the vertebral body may result. This may cause fracture and/or refracture of the endplate of the vertebral body. As a result, the local structure of the vertebral body may not be optimally stabilized.

Another shortcoming of the conventional technique is that it fails to restore a fractured vertebral body to the height of the vertebral body prior to fracture. A normal vertebral body contains two substantially planar endplates that are substantially parallel to each other. In an osteoporotic or otherwise damaged or diseased vertebral body, an endplate, or a region adjacent an endplate, fractures causing the endplates to no longer be substantially planer. The "height" between the endplates is reduced in at least a portion of the vertebral body. After a fracture, a new load condition on the back occurs. A person may accommodate the fractured state and associated pain by realigning the back through hunching or bending over. Once the fracture occurs the person will thus continue to bend over to minimize pain associated with the fracture.

A conventional vertebroplasty fails to adequately restore the lost height of the fractured vertebral body to the normal pre-fractured state. According to one known method, height restoration of the vertebral body is a purported benefit of Kyphoplasty. Kyphoplasty is a modification of vertebroplasty in which an expandable balloon is used to create a cavity in the central portion of a vertebral body before the injection of cement. In a Kyphoplasty, the expanding of the balloon within the vertebral body is said to increase the height of the vertebral body in an effort to restore it to its pre-fractured state. It has been observed that the balloon creates a cavity surrounded by a region of collapsed marrow within the vertebral body. This cavity is then filled with curable material after the balloon is removed. Although the Kyphoplasty procedure purports to restore vertebral body height, the generally spherical curable material deposit also provides only gradations of support to the endplates of the vertebral body in a manner similar to the cloud-like formation of a vertebroplasty procedure.

Another shortcoming of known methods of stabilizing a vertebral body are the effect the curative methods for a fractured vertebral body have on adjacent diseased and weakened vertebral bodies. Because the known methods create gradations of support within the vertebral body, only points or small portions of the endplates of the vertebral body are stiffened and stabilized. Localized regions of stiffness within a vertebral body create pressure points on adjacent vertebral bodies. Where those adjacent vertebral bodies are diseased or weakened, the localized regions of pressure can cause fractures in the adjacent vertebral bodies.

Additionally, in cases where an endplate of a vertebral body may be stabilized by curable material, but height has not been restored, adjacent vertebral bodies must compensate for the stiff, but misaligned vertebral body. This too may cause fractures in adjacent diseased or weak vertebral bodies.

It is also known that common curable materials intended to provide structural integrity to a damaged vertebral body, such as polymethylmethacrylate (PMMA) bone cement, possesses a level of toxicity to the body. It is preferable to minimize the use of such materials in the body to the extent possible. Non-toxic materials that may be injected into a vertebral body, such as, hydroxyapatite, calcium phosphate, antibiotics, proteins, etc., promote bone growth within the vertebral body. Such materials by themselves, however, do not generally provide enough structural integrity to an injection site on their own.

As a result, there exists a need to create a structure within the vertebral body to more fully stabilize the endplates of the vertebral body and distribute force more broadly across an endplate. The stabilization of the endplates may also be used in conjunction with methods to restore height to the vertebral body. There also exists a need to minimize the use of PMMA in the vertebral body. There also exists a need to provide patients better comfort during the procedure.

SUMMARY

In one embodiment, an apparatus for stabilizing a vertebral body is provided. The apparatus has a first curable material deposit proximal to a first endplate of a vertebral body for providing support to the first endplate of the vertebral body and a second curable material deposit proximal to a second endplate of a vertebral body for providing support to a second endplate of the vertebral body. The apparatus also has a stabilizing structure between the first curable material deposit and the second curable material deposit and connecting the first curable material deposit and the second curable material deposit for providing support to the vertebral body.

In another embodiment, a method of stabilizing a vertebral body is provided. In a first step curable material is delivered proximal to a first endplate to support the end plate. In another step, a stabilizing structure is formed between the first endplate and a second endplate to provide structural support between the first endplate and second endplate.

In yet another embodiment, a method of creating a stabilizing structure within a vertebral body is provided. In one step, a vertebral body having two endplates is accessed with an access cannula. In another step a collapsible container is inserted within the vertebral body. In another step, the collapsible container is inflated with a material such that the height of the collapsible container is at least about 80% of the height of the vertebral body between the two endplates.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

The accompanying drawings are included to provide a further understanding of the present invention and are incorporated in and are a part of this specification. Other embodiments of the present invention, and many of the intended advantages of the present invention, will be readily appreciated as they become better understood by reference to the following detailed description. The elements of the drawings are not necessarily to scale relative to each other. Like reference numerals designate corresponding similar parts.

FIGS. 34A, 34B and 34C are simplified cross-sectional views of a vertebral body showing the restoration of vertebral body height in accordance with principles of the present invention; and FIG. 35 is a simplified cross-sectional view of a vertebral body showing the restoration of vertebral body height in accordance with principles of the present invention.

DETAILED DESCRIPTION

Figure 1:
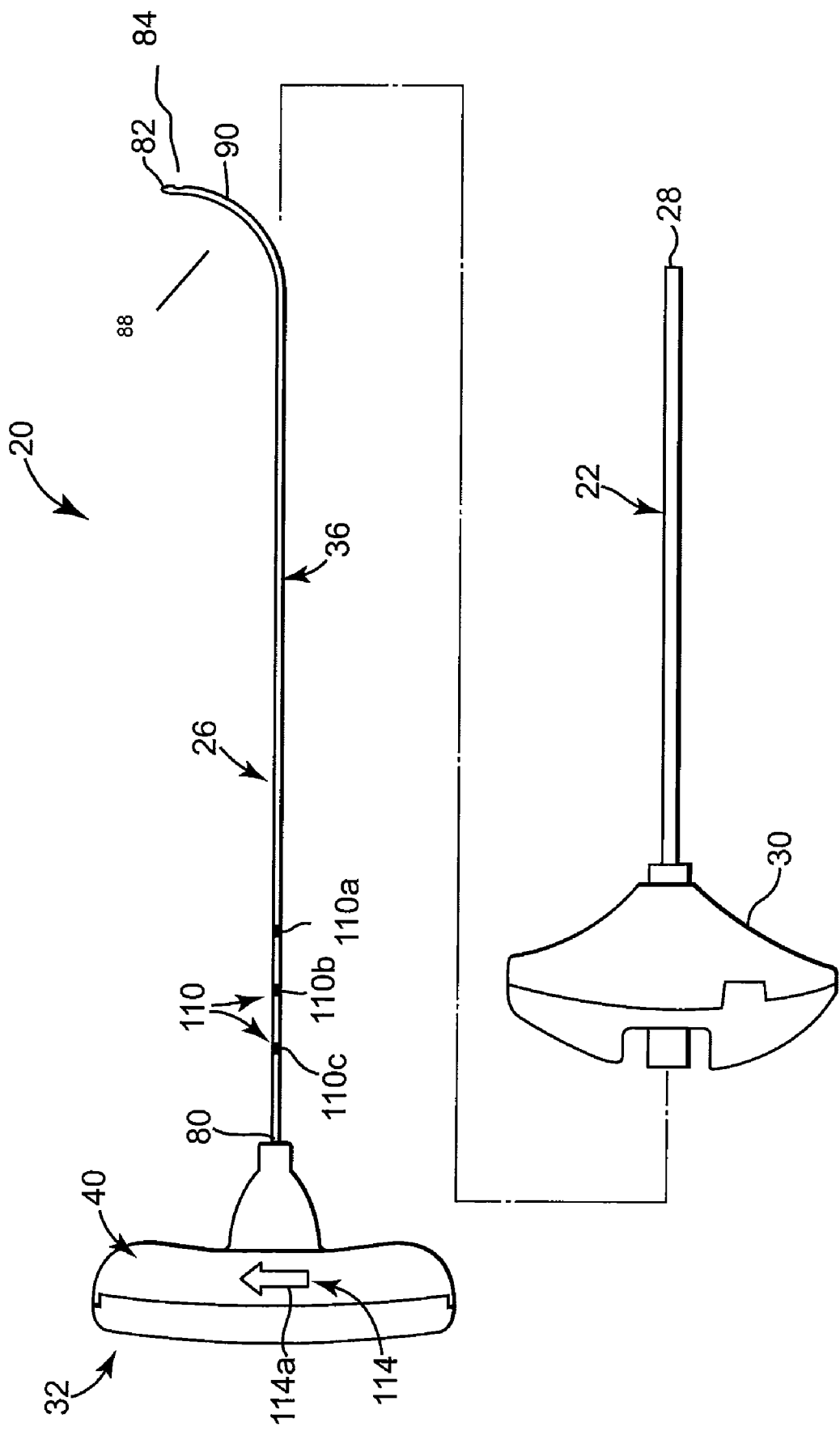
FIG. 1 is a perspective view of the curable material delivery device according to a preferred embodiment of the present invention prior to insertion of the inner section into the cannula.

FIG. 1 illustrates components of an intraosseous, curable material delivery system 20 according to one embodiment of the present invention. The system 20 includes an outer guide cannula 22 and a delivery cannula device 26 (referenced generally). Details on the various components are provided below. In general terms, however, a portion of the delivery cannula device 26 is sized to be slidably disposed within the guide cannula 22 that otherwise serves to form and/or locate a desired delivery site within bone. Once positioned, the delivery cannula device 26 is employed to inject a curable material into the delivery site. The system 20 can be used for a number of different procedures, including, for example, vertebroplasty and other bone augmentation procedures in which curable material is delivered to a site within bone, as well as to remove or aspirate material from a site within bone.

The system 20, and in particular the delivery cannula device 26, is highly useful for delivering a curable material in the form of a bone cement material. The phrase "curable material" within the context of the substance that can be delivered by the system/device of the invention described herein is intended to refer to materials (e.g., composites, polymers, and the like) that have a fluid or flowable state or phase and a hardened, solid or cured state or phase. Curable materials include, but are not limited to injectable polymethylmethacrylate (PMMA) bone cement, which has a flowable state wherein it can be delivered (e.g., injected) by a cannula to a site and subsequently cures into hardened cement. Other curable materials, such as calcium phosphates, bone in-growth material, antibiotics, proteins, etc., could be used in place of or to augment, PMMA (but do not affect an overriding characteristic of the resultant formulation having a flowable state and a hardened, solid or cured state). This would allow the body to reabsorb the cement or improve the clinical outcome based on the type of filler implant material. With this in mind, and in one embodiment, the system 20 further includes a source (not shown) of curable material fluidly coupled to the delivery cannula device 26.

Given the above, the outer guide cannula 22 generally enables access of the delivery cannula device 26 to a bone site of interest, and thus can assume a wide variety of forms. In general terms, however, the guide cannula 22 is sized to slidably receive a portion of the delivery cannula device 26, terminating in an open, distal tip 28. The distal tip 28 can further be adapted to facilitate coring of bone tissue, such as when using the guide cannula 22 to form a delivery site within bone. In some embodiments, the guide cannula 22 can further be attached, at a proximal end thereof, to a handle 30 for enhancing a surgeon's ability to manipulate the system 20. Alternatively, the handle 30 can be eliminated.

In addition, in one embodiment, the delivery cannula device 26 comprises a delivery cannula 36 that includes a deflectable segment 88 (referenced generally) defining a pre-set curve or bend 90. As described below, the deflectable segment 88, and in particular the bend 90, includes or extends from the distal end 82, and has a shape memory attribute whereby the deflectable segment 88 can be forced from the curved shape to a substantially straightened shape, and will naturally revert back to the curved shape upon removal of the force.

Further, to facilitate ready deflection of the deflectable segment 88 from the curved shape to a substantially straightened state (such as when the delivery cannula 36 is inserted within the outer guide cannula 22 (FIG. 1)) and reversion back to the curved shape, the delivery cannula 36, or at least the deflectable segment 88, is formed of a shape memory metal. In one embodiment, the delivery cannula 36 comprises Nitinol™, a known shape memory alloy of nickel (Ni) and titanium (Ti). In addition to Nitinol, other materials exhibiting this shape memory behavior can be employed, including superelastic or pseudoelastic copper alloys, such as alloys of copper, aluminum, and nickel, and alloys of copper, aluminum, and zinc, and alloys of copper and zinc. Regardless, the deflectable segment 88 is formed to be resilient and to naturally assume the desired radius of curvature. In this manner, after the delivery cannula 36, and in particular the deflectable segment 88, is flexed to a substantially straightened shape (not shown), upon a subsequent relaxation, the deflectable segment 88 "remembers" the pre-set curved shape and reversibly relaxes/returns to the bend 90.

In the embodiment shown in FIG. 1, a side orifice 84 is formed adjacent the distal end 82, extending through a thickness of a sidewall of the delivery cannula 36. In this embodiment, a single orifice 84 is provided, and is located "opposite" a direction of the bend 90. Curable material can be delivered to the interior of a vertebral body through the side orifice 84 of the delivery cannula 36 shown in FIG. 1. As will be discussed in more detail below, other orifice configurations may be used to deliver curable material to the interior of a vertebral body. As will also be discussed in more detail below, the curved delivery cannula 36 can be used to create voids within soft body material within the vertebral body by inserting the curved delivery cannula into the vertebral body and rotating it about the delivery cannula's longitudinal axis and/or moving the curved delivery cannula in a reciprocating manner.

Figure 2:
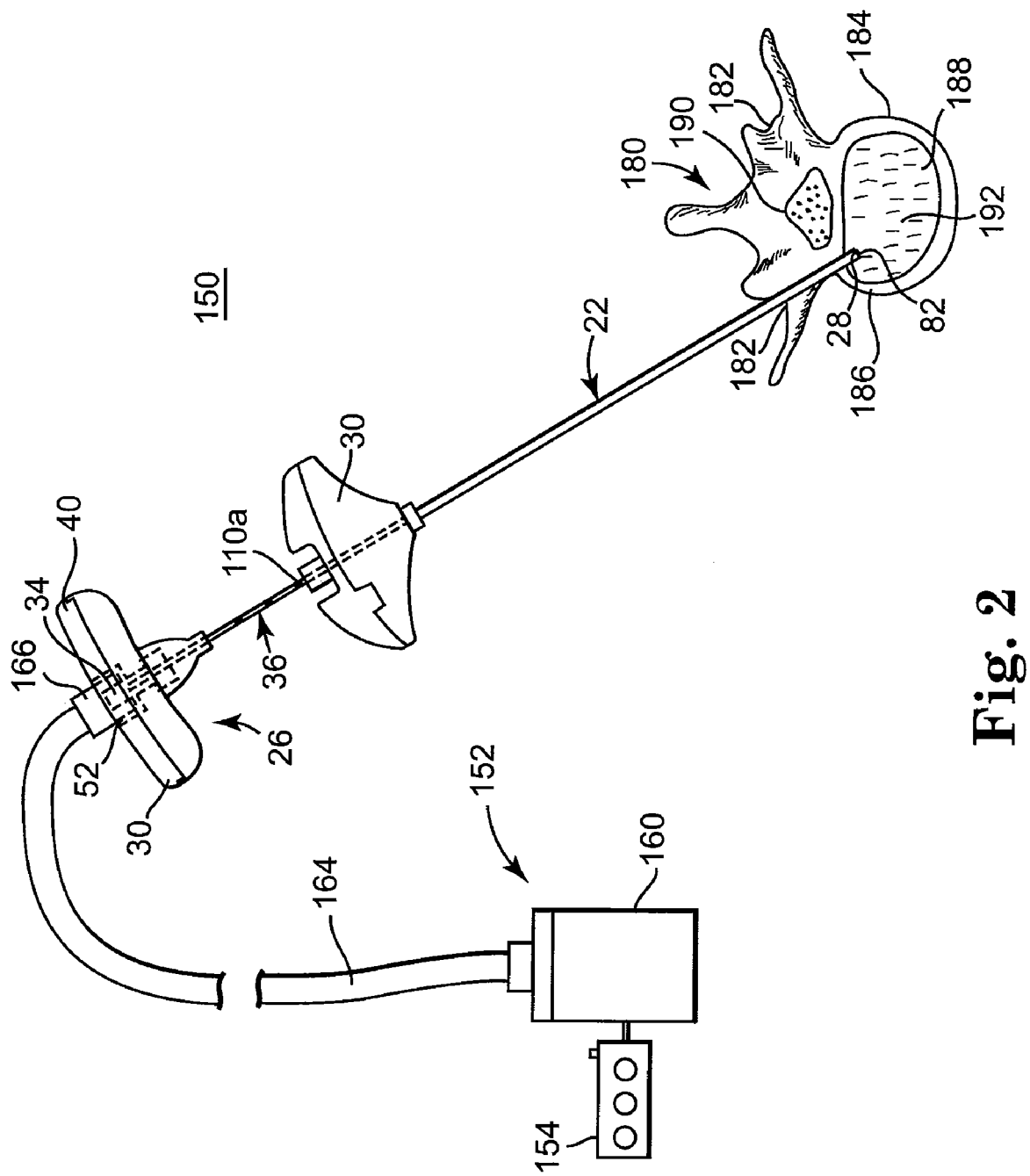
FIG. 2 is a perspective view of the curable material delivery device according to a preferred embodiment of the present invention after insertion of the inner section into the cannula.

Regardless of an exact configuration, the assembled delivery cannula device in accordance with principles of the present invention is highly useful in performing a wide variety of bone stabilizing procedures as part of an overall curable material delivery system. To this end, FIG. 2 illustrates an intraosseous curable material delivery system 150 according to one embodiment of the present invention, employed to perform a vertebroplasty procedure. The system 150 includes the outer guide cannula 22, the delivery cannula device 26, a curable material source 152 fluidly coupled to the delivery cannula device 26, and a controller 154 coupled to at least the curable material source 152.

The curable material source 152 includes, in one embodiment, a canister 160 containing a curable material as previously described, and tubing 164 extending from the canister 160 to the handle assembly 30 of the delivery cannula device 26. In this regard, the tubing 164 terminates at a fitting 166 configured to removably attach to the hub 34. In particular, the fitting 166 is configured to fit within the passage 52 of the handle 40 and removably couple to the hub 34.

The controller 154 can assume any form known in the art and is coupled to the curable material source 152. In an exemplary embodiment, the controller 154 controls a mass flow and a mass flow rate (i.e., a fluid delivery rate) of curable material from the canister 160 to the delivery cannula device 26. The controller 154 can include a variety of actuators (e.g., switch(es), foot pedal(s), etc.) affording a user the ability to remotely control liquid flow into the delivery cannula 36.

Alternatively, manual control can be employed such that the controller 154 can be eliminated.

During a palliative bone procedure, with the delivery cannula 36 partially retracted within, or entirely removed from, the outer guide cannula 22, the outer guide cannula 22 is located at a desired delivery site within bone. For example, in a vertebroplasty procedure the outer guide cannula 22 is introduced into a vertebra 180, preferably at a pedicle 182. In this regard, the vertebra 180 includes a vertebral body 184 defining a vertebral wall 186 surrounding bodily material (e.g., cancellous bone, blood, marrow, and other soft tissue) 188. The pedicle 182 extends from the vertebral body 184 and surrounds a vertebral foramen 190. In particular, the pedicle 182 is attached posteriorly to the vertebral body 184 and together they comprise the vertebrae 180 and form the walls of the vertebral foramen 190. As a point of reference, the intraosseous system 150 is suitable for accessing a variety of bone sites. Thus, while a vertebra 180 is illustrated, it is to be understood that other bone sites can be accessed by the system 150 (i.e., femur, long bones, ribs, sacrum, etc.).

The outer guide cannula 22 forms an access path to a delivery site 192 (or forms the delivery site 192) through the pedicle 182 into the bodily material 188. Thus, as illustrated, the outer guide cannula 22 has been driven through the pedicle 182 via a transpedicular approach. The transpedicular approach locates the outer guide cannula 22 between the mammillary process and the accessory process of the pedicle 182. In this manner, the outer guide cannula 22 provides access to the delivery site 192 at the open, distal tip 28. With other procedures, the outer guide cannula 22 can similarly perform a coring-like operation, forming an enlarged opening within bone. In one preferred embodiment illustrated in FIG. 2, the distal tip 28 of the guide cannula 22 is positioned close to the entrance point into the delivery site 192. As will be explained in more detail herein, the smaller the projection of the distal tip 28 into the delivery site 192 allows for greater access for the delivery cannula 36 to be positioned within the delivery site 192 and deliver curable material to desired locations within the delivery site 192.

Once the outer guide cannula 22 has formed, or is otherwise positioned within bone at, the desired delivery site 192, the delivery cannula 36 is slidably inserted/distally advanced within the outer guide cannula 22. As illustrated generally in FIG. 2, the distal end 82 of the delivery cannula 36 is poised at the distal tip 28 of the outer guide cannula 22. Approximate alignment of the first depth marking 110*a* with the handle 30 provides a user with visual confirmation (at a point outside of the patient) of the distal end 82 positioning relative to the outer guide cannula 22 distal tip 28. Prior to further distal movement, the delivery cannula 36 is entirely within the outer guide cannula 22 such that the deflectable segment 88 of the delivery cannula 36 is constrained (i.e., flexed) to a substantially straightened shape that generally conforms to a shape of the outer guide cannula 22. A force is effectively imparted by the guide cannula 22 onto the deflectable segment 88 due to the radius of curvature defined by the deflectable segment 88 in a "natural" state being larger than an inner diameter of the guide cannula 22. This interaction essentially "removes" the pre-set curvature of the bend 90, forcing or rendering the deflectable segment 88 to a substantially straightened state (it being understood that because an inner diameter of the guide cannula 22 is greater than the outside diameter of the delivery cannula 36, the deflectable segment 88 will continue to have a slight curvature within the guide cannula 22; thus, "substantially straightened" is in reference to the delivery cannula 36 being substantially, but not necessarily entirely, linear). Thus, prior to interaction with the delivery site 192 (FIG. 2), the delivery cannula 36 is flexed in a substantially straight, non-curved orientation within the outer guide cannula 22.

Figure 3:
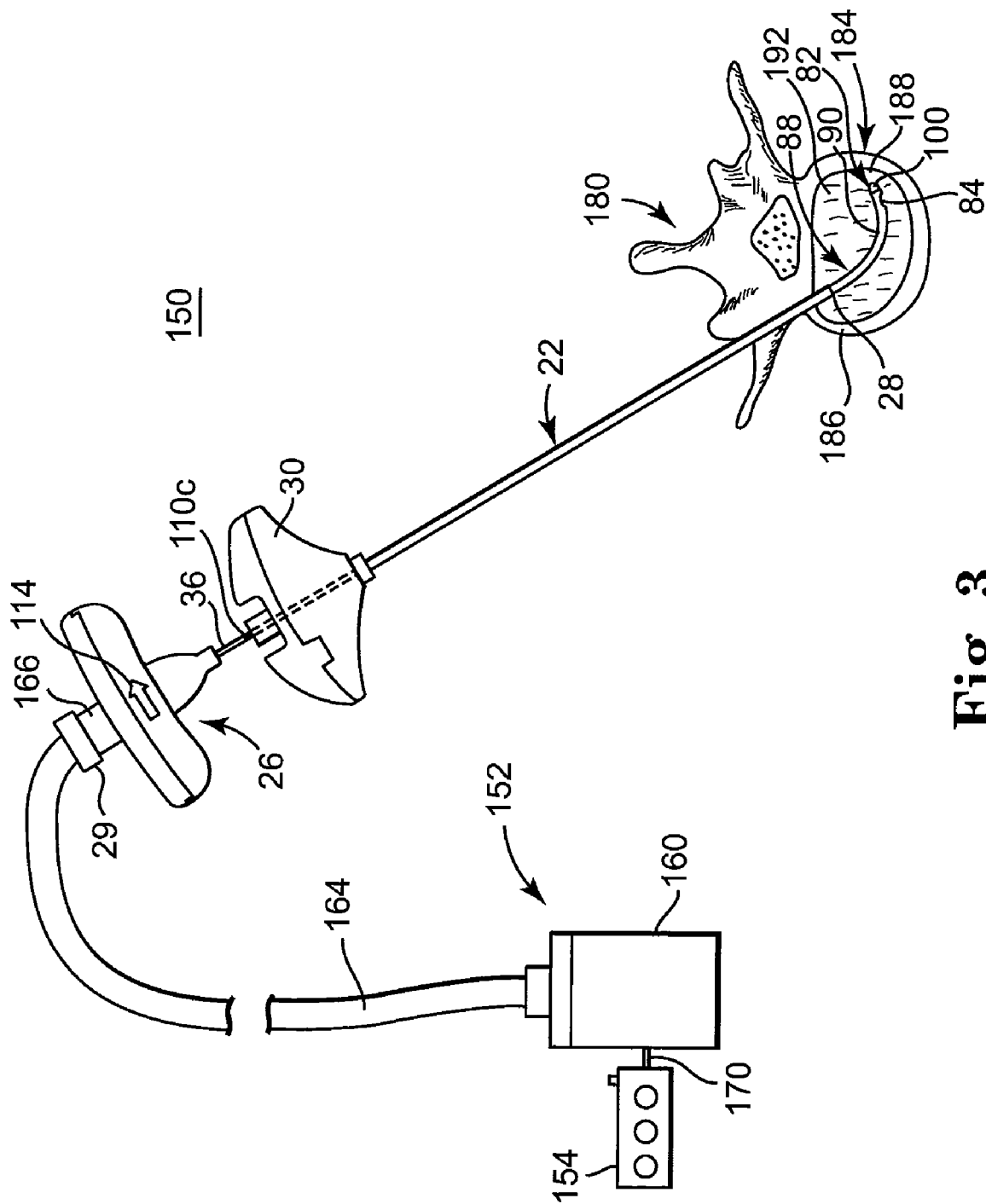
FIG. 3 is a perspective view of the curable material delivery device according to a preferred embodiment of the present invention after insertion of the inner section into the cannula.

The delivery cannula device 26, and in particular the delivery cannula 36, is then distally advanced within the guide cannula 22 as shown in FIG. 3. In particular, the delivery cannula 36 is distally maneuvered such that at least a portion of the deflectable segment 88 extends beyond the open tip 28 of the guide cannula 22 and into the delivery site 192. The now unrestrained portion of the deflectable segment 88 naturally deflects laterally (from the substantially straight shape described above) upon exiting the guide catheter 22, reverting to the pre-set curvature of the bend 90 previously described due to the shape memory characteristic. The user can visually confirm a length of distal extension of the delivery catheter 36 from the guide catheter 22 via a longitudinal positioning of the indicia 110*b* or 110*c* (the indicia 110*c* being visible in FIG. 3) relative to the handle 30. Further, the directional indicia 114 indicates to a user (at a point outside of the patient) a spatial direction of the bend 90 within the delivery site 192 relative to a spatial position of the handle 40.

In connection with distal advancement of the delivery cannula 36, the blunt tip 100 of the distal end 82 is hemispherically shaped (or other non-sharpened or blunt shape) and thus atraumatic relative to contacted tissue/bone. In this manner, the blunt tip 100 can contact and/or probe the vertebral wall 186 with a minimum of risk in puncturing or coring the vertebral body 184. Thus, the blunt tip 100 offers an advantage over the conventional, sharp-edged bone cement delivery needles, and does not require a separate wire to prevent coring as is otherwise necessary with available curved needles.

The side orifice 84 is offset from the distal end 82 and is, therefore, available to deliver curable material into, and remove bodily material from, the delivery site 192. In particular, the side orifice 84 can eject curable material radially from, and aspirate bodily material into, the delivery cannula 36, even when the distal end 82 is pressed against a surface, such as an interior wall of the vertebral body 184.

Figure 4A:
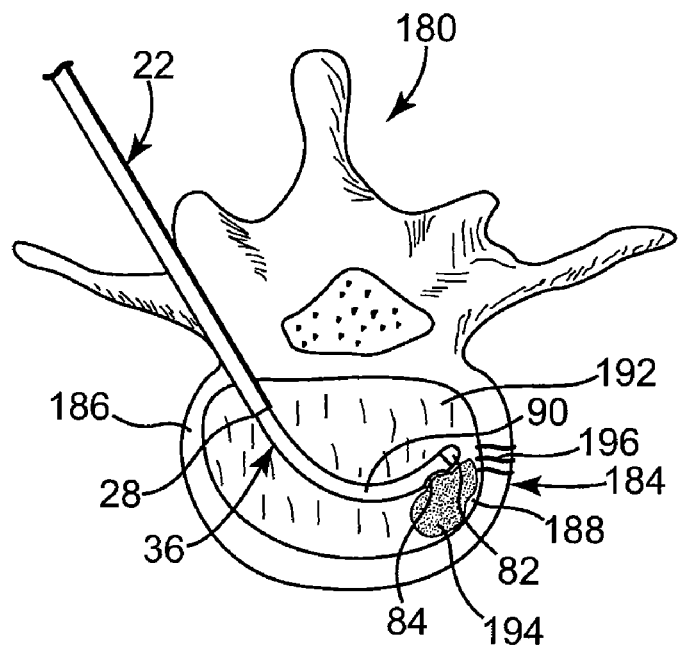
FIGS. 4A and 4B are partial cross-sectional views of a vertebral body, illustrating use of the system in accordance with principles of the present invention.
Figure 4B:
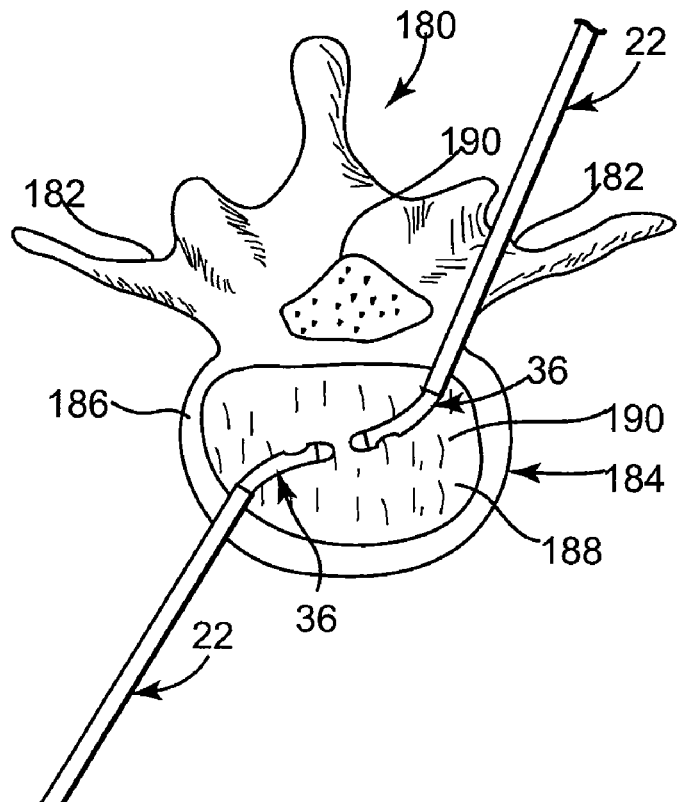
Figure 5A:
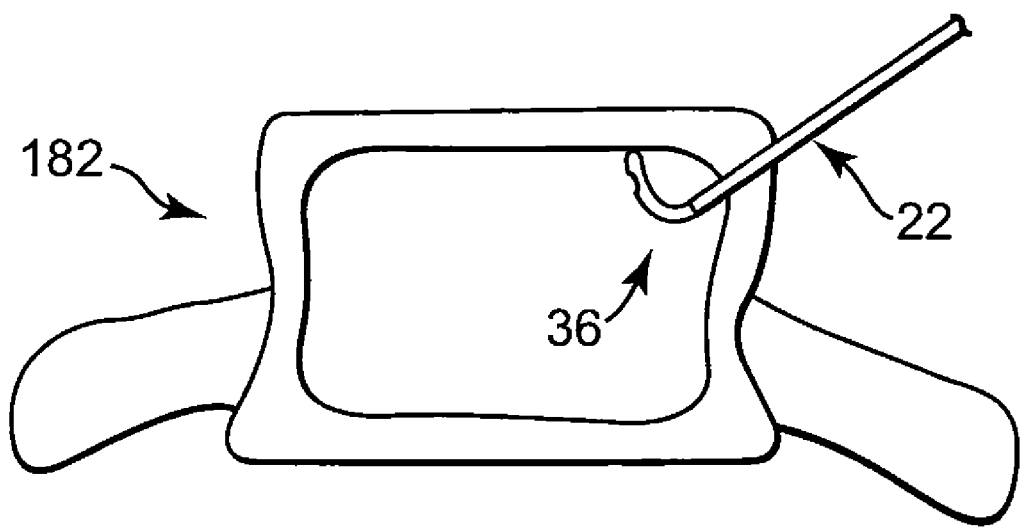
FIGS. 5A and 5B are partial cross-sectional views of a vertebral body, illustrating use of the system in accordance with principles of the present invention.
Figure 5B:
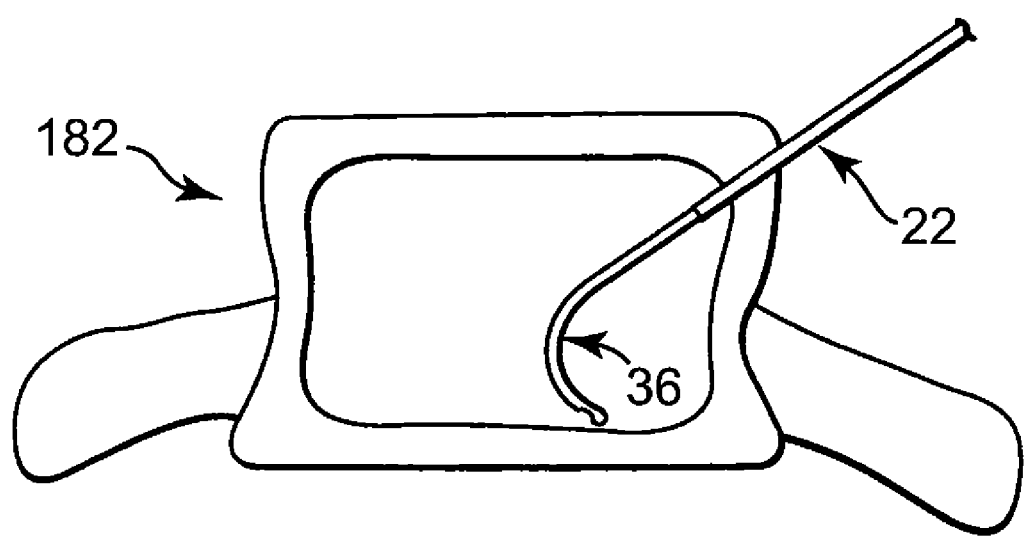

With the above in mind, in one embodiment, general delivery of curable material to a vertebral body is shown in FIGS. 4A-4B. The fluid source 152 is operated (e.g., via the controller 154) to deliver a curable material (not shown) to the delivery cannula 36 via the hub 34. Curable material entering the delivery cannula 36 is forced through the lumen 86 towards the side orifice 84. As shown in FIG. 4A, the curable material is then dispensed/injected from the delivery cannula 36 in a radial fashion from the side orifice(s) 84 and into the delivery site 192 in a cloud-like pattern 194. Alternatively or in addition, the delivery site 192 can be aspirated by replacing the curable material source 152 with a vacuum source (not shown).

In another embodiment, curable material is delivered to the delivery cannula 36 prior to introducing the delivery cannula 36 into the guide cannula 22. In practice, an operator may advance curable material beyond the side orifice(s) 84 the delivery cannula 36 in order to completely fill the delivery cannula 36 and then wipe the side orifice(s) 84 of excess curable material before insertion into the guide cannula 22. The delivery cannula 36 is thus preloaded with curable material before the delivery cannula 36 is connected with the guide cannula 22. Once the delivery cannula 36 is inserted into the guide cannula 22 curable material is immediately available to be delivered into the implantation site.

Importantly, by injecting the curable material radially from a side of the delivery cannula 36 rather than axially from the distal most end (as will otherwise occur with conventional delivery needles), the system 150 (FIG. 4A) can avoid forcing the curable material into a fracture or other defect that may in turn lead to undesirable leaking of the curable material through the fracture. By way of example, FIG. 4A illustrates a fracture 196 in the vertebral body wall 186. Vertebroplasty is a common solution to such vertebral fractures, with the accepted repair technique entailing positioning the distal end 82 at or "facing" the fracture 196 to ensure that the curable material is dispensed in relatively close proximity thereto. With known delivery needles, this preferred approach results in the curable material being injected directly toward the fracture 196. In contrast, with the delivery catheter 36 of the present invention, the distal end 82 is still "facing" the fracture 196, yet the injected curable material cloud 194 is not forced directly toward the fracture 196. Instead, the curable material cloud 194 indirectly reaches the fracture 196 with minimal retained propulsion force such that the curable material cloud 194 is unlikely to forcibly "leak" through the fracture 196. However, the delivery site 192 is, as a whole, still filled with the curable material cloud 194 to effectuate the desired repair.

As shown in FIG. 4A, an entirety of the delivery site 192 is substantially accessible by the delivery cannula 36. To this end, while the guide cannula 22 has been inserted via a right posterior-lateral approach, the system 150 can effectuate a vertebroplasty procedure from a left posterior lateral approach, or to right or left anterior lateral approaches as shown in FIG. 4B.

In one embodiment, and returning to FIG. 4A, a desired volume of the curable material is delivered entirely through the delivery cannula 36. In other embodiments in accordance with principles of the present invention, after injecting a first volume of curable material through the delivery cannula 36, the delivery cannula 36 is disconnected from the curable material source 152 and removed from the guide cannula 22. The curable material source 152 is then fluidly connected to the guide cannula 22 (e.g., the fitting 166 is fluidly connected to a corresponding fluid port/hub provided with the handle 30) and then operated to inject a second volume of curable material to the delivery site 192 via the guide cannula 22.

Figure 6A:
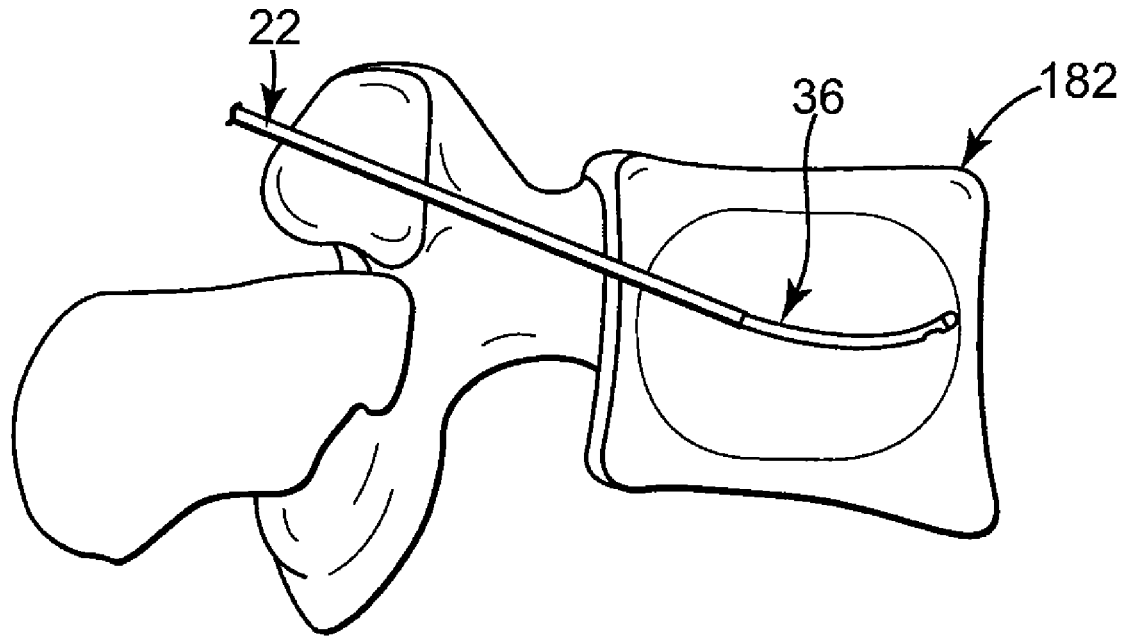
FIGS. 6A and 6B are partial cross-sectional views of a vertebral body, illustrating use of the system in accordance with principles of the present invention.
Figure 6B:
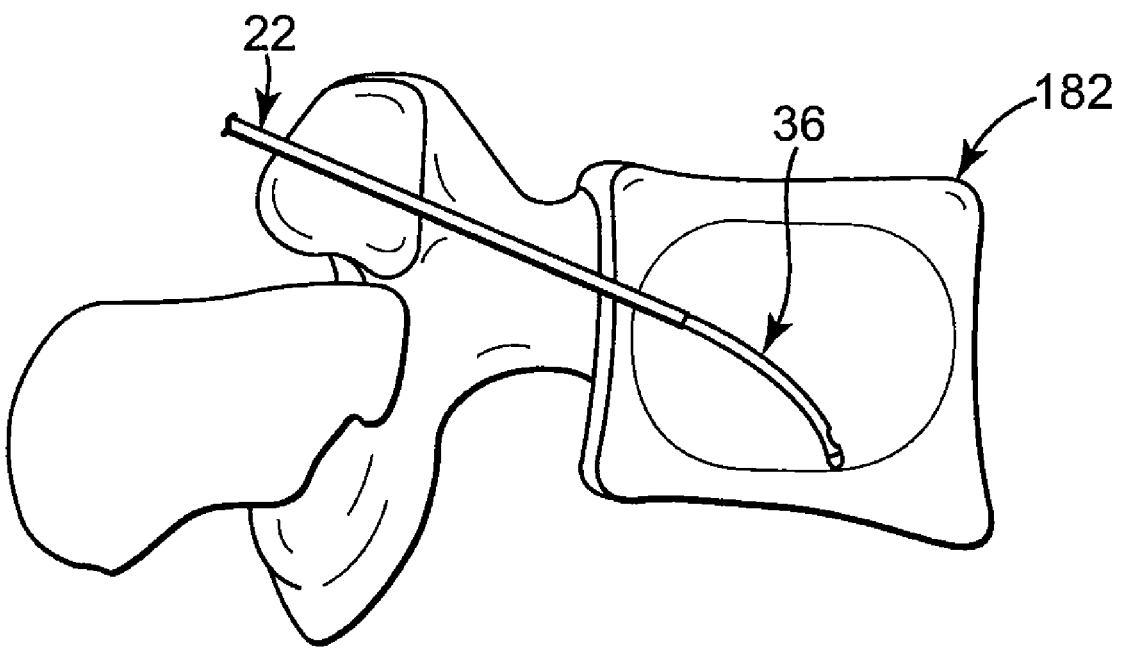

In more general terms, during the palliative bone procedure, a clinician operating the intraosseous system 150 extends a portion of the pre-set curve 90 into the delivery site 192 otherwise defined within bone. In one embodiment, a subsequent rotation of the delivery cannula 36 rotates a spatial position of the side orifice 84 relative to the delivery site 192, thus accessing multiple planes of the delivery site 192 with only one "stick" of the outer guide cannula 22. Thus, by a combination of retracting the delivery cannula 36 within the outer guide cannula 22, distally advancing the delivery cannula 36 relative to the outer guide cannula 22, and by rotating the delivery cannula 36, multiple planes and multiple regions of the bone site of interest can be accessed by the delivery cannula 36 with a single approach of the outer guide cannula 22. Thus, for example, a unipedicular vertebroplasty can be accomplished with the system 150. FIGS. 5A-6B generally illustrate (FIGS. 5A and 5B from an anterior perspective; FIGS. 6A and 6B from a left lateral perspective) various planes/regions of the vertebral body 182 accessible with rotation and/or advancement of the delivery cannula 36 relative to the guide cannula 22 (again with the guide cannula 22 remaining stationary). Notably, in the drawings of FIGS. 5A-6B, a direction of the bend defined by the delivery cannula 36 is not necessarily perpendicular to the plane of the page, such that the bend may not be fully evident in each view.

Figure 7:
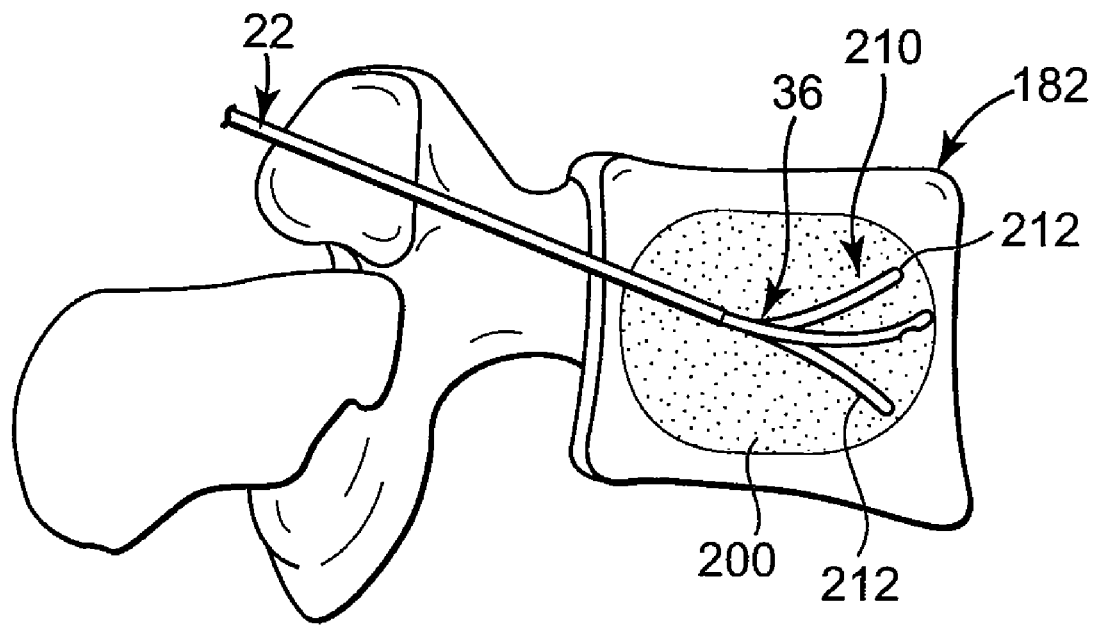
FIGS. 7 and 8 are partial cross-sectional views of a vertebral body, illustrating use of the system in accordance with principles of the present invention.
Figure 8:
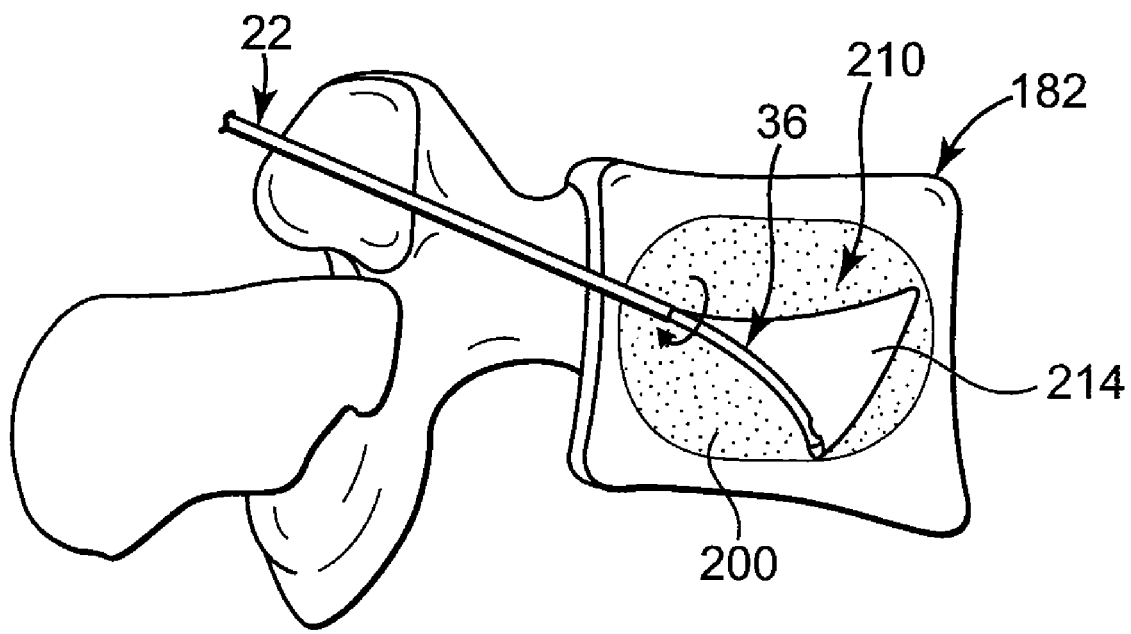

With reference to FIGS. 7-8, another preferred method for delivering curable material is depicted. In this preferred embodiment, a clinician creates voids 210 in soft body material 200 (e.g., cancellous bone, blood, marrow, and other soft tissue) within a bone delivery site by manipulating the delivery cannula 36. The voids 210 can then be filled with curable material. It has been observed that when voids are created, curable material delivered to the delivery site will generally flow into the voids 210 instead of the soft body material 200. As a result, a clinician can create a void 210 at a relatively small desired area, and fill primarily just that area with curable material.

According to one preferred embodiment, voids can be created through a combination of retracting the delivery cannula 36 within the outer guide cannula 22 and distally advancing the delivery cannula 36 relative to the outer guide cannula 22, thus moving the delivery cannula 36 in a reciprocating manner. The reciprocating action causes the delivery cannula 36 to crush the soft body material and create a channel 212 within the soft body material. Additionally, by retracting the delivery cannula 36 within the outer guide cannula 22 and rotating the delivery cannula 36 so that the bend will distally advance within the delivery site at a different orientation, the delivery cannula 36 can create multiple channels 212 within the soft body material 200. Further, the delivery cannula 36 may be advanced distally only partially within the delivery site and then removed to create shorter channels 212 within the implantation site where desired.

According another preferred embodiment shown in FIG. 8, the delivery cannula 36 can be rotated or spun after introduction into the implantation site. The rotating or spinning of the delivery cannula 36 causes it to rotate or spin within the delivery site and whip through soft body material 200 to create a cone-shaped void 214 in the soft tissue 200 within the delivery site. Cone-shaped voids 214 of various sizes may be created by only partially inserting delivery cannula 36 into the implantation site and rotating the delivery cannula 36.

Voids 210 within the soft body material of various sizes and shapes can be created by using a combination of the above disclosed methods. According to one preferred method, a physician may introduce curable material within the implantation site as he or she is creating the voids within the implantation site. Thus, the voids may be created and filled at the same time.

With the above principles in mind, voids can be created and/or curable material can be delivered in a manner that allows a clinician to place curable material within a vertebral body with more precision and create desired formations of curable material to stabilize the vertebral body.

Figure 9A:
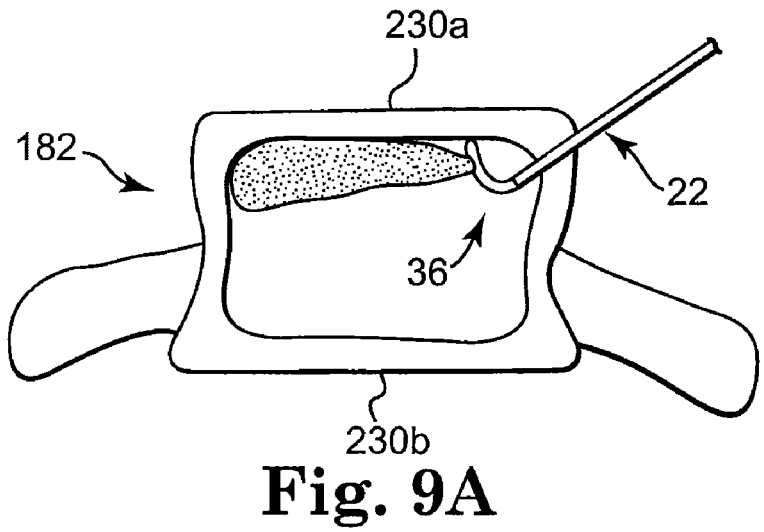
FIGS. 9A, 9B and 9C are partial cross-sectional views of a vertebral body, illustrating use of the system in accordance with principles of the present invention.
Figure 9B:
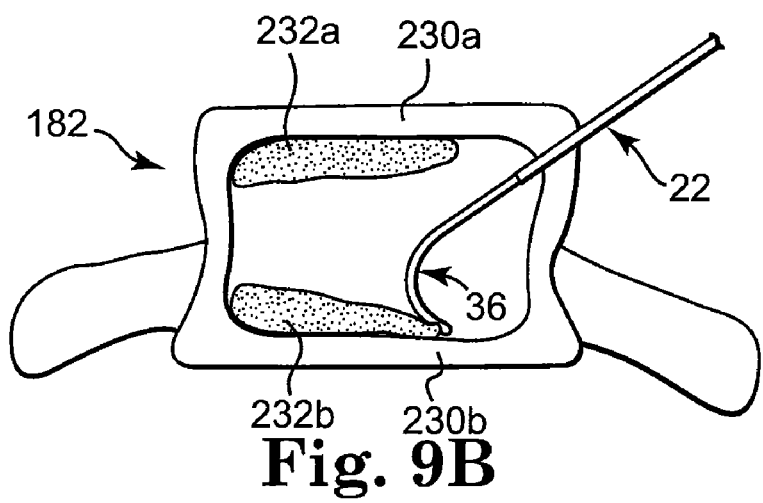

In one embodiment, curable material can be delivered in different planes to form curable material structures within the cavity to stabilize the endplates of the vertebral body, as depicted in FIGS. 9A and 9B. In one preferred embodiment, curable material 232a and 232b is deposited proximal to the endplates 230a and 230b of the vertebral body so that the curable material substantially interfaces with the endplates 230a and 230b and provides structural support. According to one preferred embodiment, the procedure leaves a region between the curable material deposits 232a and 232b that contains substantially no curable material. Curable material can thus be deposited in only a particular region or regions of the cavity.

In the embodiment of FIGS. 9A and 9B, the curved delivery cannula 36 necessarily creates voids (not depicted) as the end of the curved delivery cannula 36 is repeatedly manipulated proximal to the endplates to create the desired curable material formations in the desired locations. One of skill in the art will understand that the creation of voids with the curved delivery cannula 36 and the injection of curable material can occur simultaneously or can occur in separate steps. As will be discussed in more detail below, where voids are created in a separate step, other apparatuses and methods may be used to create voids within the vertebral body.

Figure 10A:
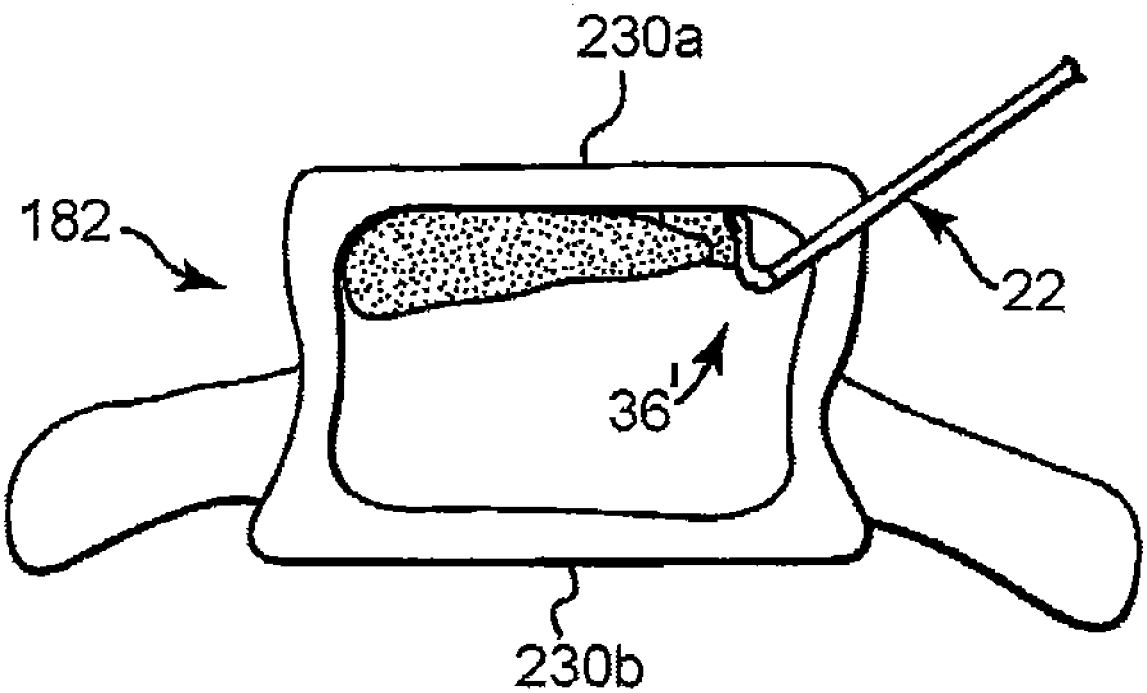
FIGS. 10A and 10B are partial cross-sectional views of a vertebral body, illustrating use of the system in accordance with principles of the present invention.
Figure 10B:
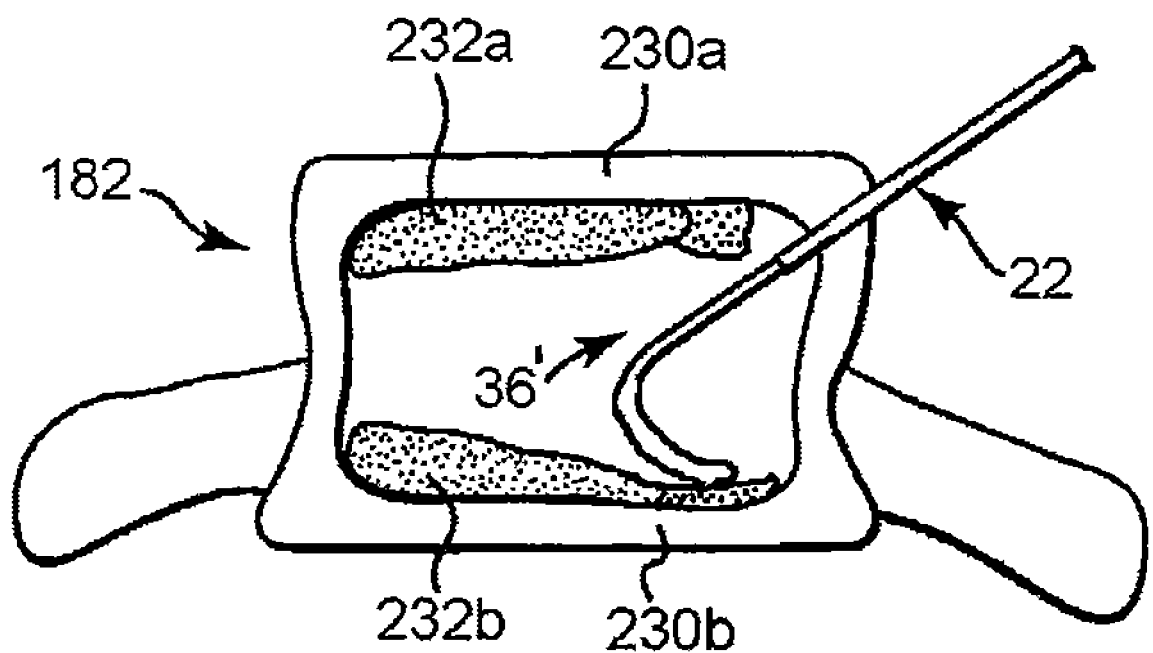

In another embodiment depicted in FIGS. 10A-10B, the clinician may use a second delivery cannula 36' having a different radius of curvature than the delivery cannula 36 curve of FIGS. 9A-9B. The different curves provide a clinician more flexibility to place the tip of the delivery cannula 36' in greater locations within the vertebral body. This also allows the clinician to place additional volumes of curable material, or place volumes of curable material more precisely, within the vertebral body. While two different cannulas are shown in FIGS. 10A-10B, more than two cannulas having different curvatures may also be used.

Figure 9C:
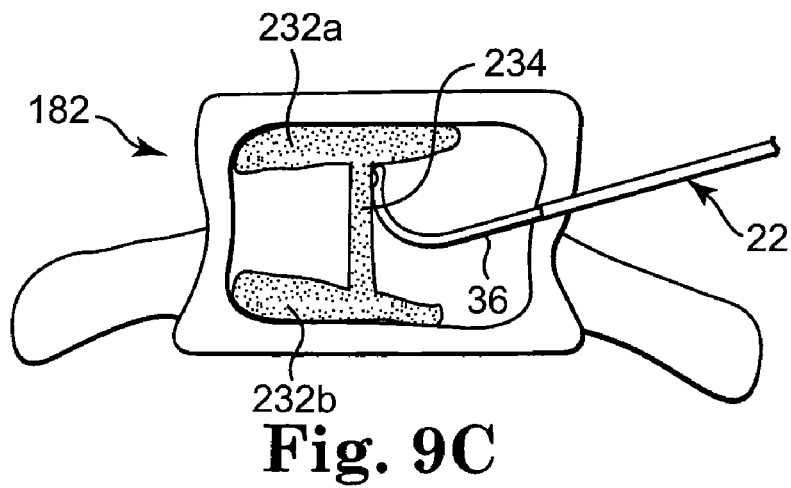

With reference to FIG. 9C, in another preferred embodiment the curable material deposits 232a and 232b can be connected by placing curable material between the curable material deposits 232a and 232b to form a curable material stabilizing column 234. In this embodiment, curable material deposits 232a and 232b are first created to stabilize the endplates of the vertebral body. A stabilizing curable material column 234 is then created between the curable material deposits 232a and 232b to connect the curable material deposits and form a curable material structure within the vertebral body. By first stabilizing the endplates, deformities created due to compression fractures can be stabilized. By stabilizing both endplates and then creating a column type structure between the endplates, the vertebral body stiffness may be significantly increased thereby minimizing issues of the overall strength of the vertebral body. It has been observed that depositing curable material in the known methods of depositing material in the center of the vertebral body, as typically created by a Kyphoplasty procedure, or dispersed throughout the vertebral body, as typically created by a vertebroplasty procedure, do not uniformly strengthen the vertebral body. Because the cement is concentrated in regional areas, there is only minimal stabilization of the endplates. By stabilizing both endplates and then providing a structure to secure them together, the repaired vertebral body stiffness will better approximate the normal stiffness of a non-fractured vertebral body when compared to the known vertebroplasty or kyphoplasty procedures. In another preferred embodiment, if the compression fracture is more pronounced on one endplate, stabilization of only that one endplate may be necessary and only one curable material deposit will be created proximal to the vertebral endplate. In this embodiment, a support structure may be created to connect the curable material deposit and the vertebral endplate opposite the vertebral endplate being repaired.

The formation of stabilizing structures, creation of voids and delivery of curable material have been described above with respect to the use of a curved delivery cannula. Other apparatuses and methods, whether instead of or in conjunction with a curved delivery cannula, may also be employed to perform these functions in accordance with the principles taught herein.

Stabilization

Figure 11A:
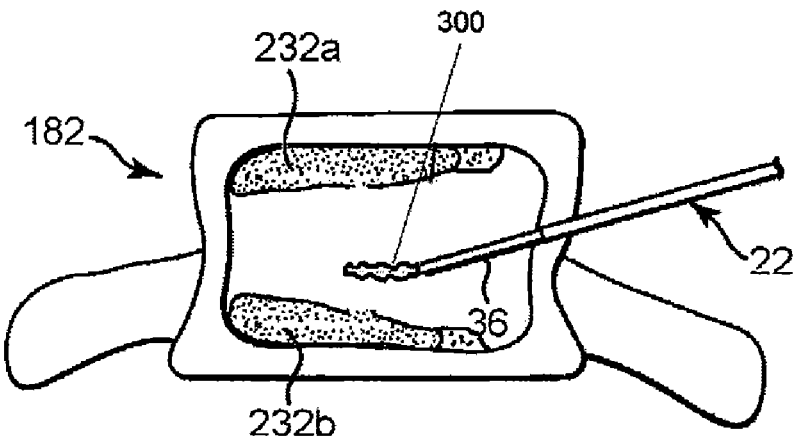
FIGS. 11A, 11B and 11C are partial cross-sectional views of a vertebral body, illustrating use of the system in accordance with principles of the present invention.
Figure 11B:
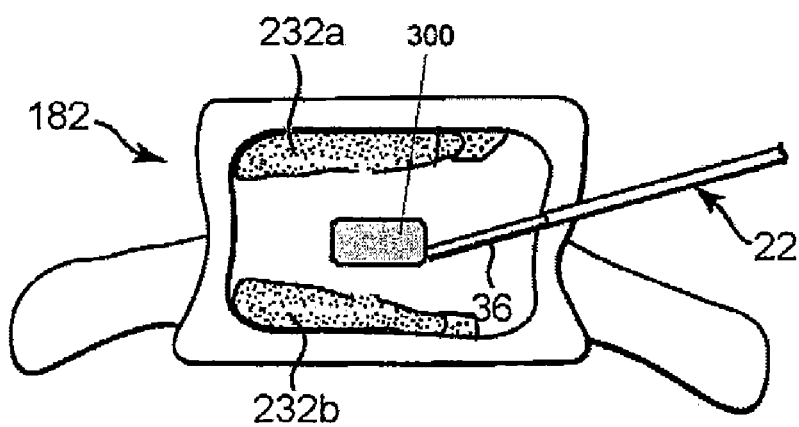
Figure 11C:
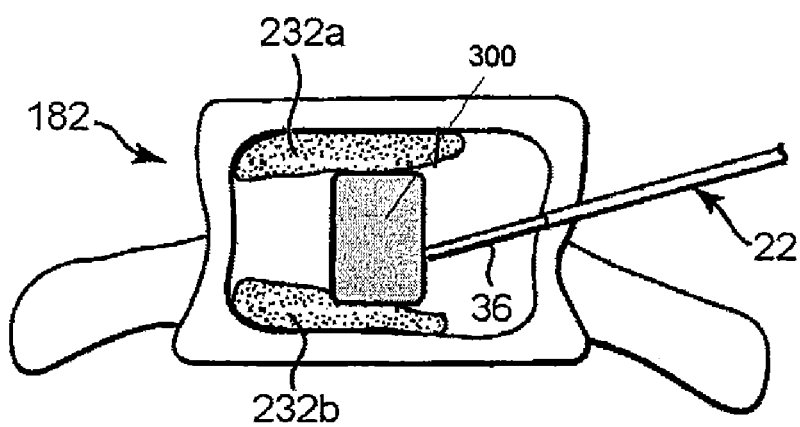

With reference to FIGS. 11A-11C, another embodiment of an apparatus and method to provide structural integrity to a vertebral body is shown. In this embodiment a collapsible container 300 may be filled with curable material to support deposits 232a and 232b. In one embodiment, the collapsible container 300 can be filled with a curable material having significant structural integrity, such as PMMA. The container 300 restricts the flow of curable material so that curable material does not migrate substantially beyond the container 300. The curable material also then cures in a desired shape and provides structural support.

In another embodiment, curable materials lacking significant structural integrity, such as hydroxyapatite or calcium phosphate bone in-growth material, can be placed within the collapsible container 300. Such materials, on their own, do not provide significant structural integrity as, for example, PMMA. The materials tend to be too brittle when cured to provide desired integrity. The collapsible container 300, however, provides additional structural integrity to the curable material. The collapsible container 300 effectively holds the material together, which results in a stronger structure than without the use of a collapsible container 300. Further, use of such curable materials promotes bone formation within the vertebral body and, thus, acts to restore the vertebral body closer to its pre-fracture state compared to the use of structurally stiffer PMMA. It has been observed that use of a porous collapsible container 300, such as a mesh bag, with bone in-growth material causes tissue within the vertebral body to interdigitate with the mesh bag containing the bone in-growth material. In this way, the bone in-growth material promotes tissue growth outside of the mesh bag, leading to bone tissue growth inward into the mesh bag. Such interdigitation further promotes formation of a relatively strong structure within the vertebral body.

In one embodiment of the container 300, a bag can be made out of a DACRON™ mesh; however, other materials capable of withstanding high pressures may also be used. In another embodiment, mesh material of poly(ethylene terephthalate) (PET) may be used. In one embodiment, the mesh bag is preferably between about 15 mm and about 30 mm to accommodate various sizes of vertebrae and fractures. The fibers of the mesh may be woven into a loose weave that is 50×55 fibers per cm$^2$. The average pore dimensions may be 0.143 mm×0.146 mm (machine direction×cross direction), resulting in a pore area of 0.021 mm$^2$.

In the operation of a preferred embodiment, curable material deposits 232a and 232b are first delivered proximal to the endplates of the vertebral body according to the methods described herein. The collapsible container 300 is then inserted into the vertebral body through the delivery cannula 36 and inflated between the curable material deposits 232a and 232b. The collapsible container 300 is preferably of sufficient size so that when the collapsible container 300 is inflated, it engages the curable material deposits 232a and 232b and thus provides support to the material deposits. In one preferred embodiment, the height of the container is at least about 80% of the height of the vertebral body between the two end plates.

In another embodiment, the container 300 is first inflated within the vertebral body. Curable material may then be deposited between the ends of the container 300 and the endplates of the vertebral body to form curable material deposits 232a and 232b that stabilize the vertebral body endplates.

In another embodiment, voids within the soft tissue may be created by the inflation of the container 300 itself. During a procedure, an empty or collapsed container 300 is first inserted into the vertebral body. The container 300 is then inflated within the vertebral body causing the soft body material proximal to the bag to be crushed. Inflation of the container 300 thus causes the creation of a void within the soft body material in the vertebral body. According to one embodiment, the container 300 is inflated hydraulically using a liquid, such as saline. Other liquids may also be used. In this embodiment the liquid can be removed from the container 300, which then can then be filled with material, such as bone in-growth material. In another embodiment, the container 300 can be removed and curable material is filled into the void created by the container 300. In another embodiment, the container 300 is inflated using curable material such as PMMA or bone in-growth material. In this embodiment, the steps of creating a void and delivering the desired material can be performed at the same time. Also, in this embodiment, the desired material can be deposited within a vertebral body in a specific desired shape according to a predetermined shape of the container.

In another embodiment, a void is first created in the location of where the container 300 will be placed prior to insertion of the container 300. A void may be created through the use of the curved delivery cannula 36, as described above, or with any of the other structures or methods of creating a void described herein.

In another embodiment, the container 300 may also be used without the formation of curable material deposits 232a or 232b. In this embodiment, the container has suitable height to engage the endplates of the vertebral body and has suitable surface area engagement with the endplates to distribute the load forces across a relatively wide area of the endplate.

In another embodiment, the container 300 may be preformed into a variety of desired shapes to create voids and/or create curable material structures within the vertebral body having the desired shapes. In the embodiment of FIGS. 11A-11C, the container 300 is generally cylindrical. In this embodiment, the container 300 is positioned within the vertebral body so that upon inflation, the substantially planar ends of the cylindrical container 300 may engage and support the material deposits or endplates of the vertebral body. The container 300 may be placed and oriented within the vertebral body before inflation to achieve a desired location of the void and/or container 300 within the vertebral body upon inflation. Other container 300 shapes such as generally box-shaped, cubic, trapezoidal, "H" shaped or shaped in a generally spoke-like pattern may also be used.

One skilled in the art will also appreciate that the container 300 may also be used to restore height to the vertebral body. Use of a container 300 that is of a height that is greater than the cavity height of the fractured vertebral body may be restored to prefracture height upon inflation of the bag.

Figure 12:
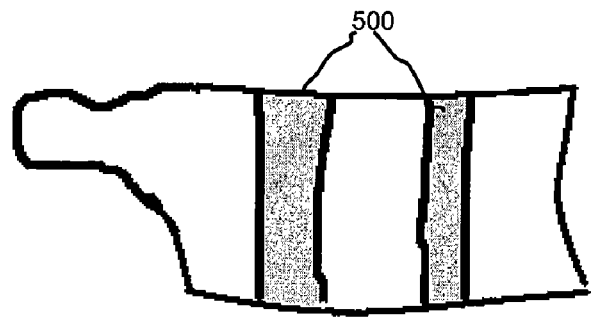
FIG. 12 is a simplified cross-sectional view of a vertebral body having a stabilizing structure in accordance with principles of the present invention.

In additional to the apparatuses and methods described herein, several other structures may provide structural integrity to endplates of a vertebral body. In one embodiment depicted in FIG. 12, a clinician may create one or more columns of curable material 500 between the endplates of the vertebral body without first stabilizing the endplates of the vertebral body with curable material. The one or more columns may distribute forces and a greater surface area than a single column. The one or more columns may also be used to provide support to one or more curable material deposits.

Figure 13:
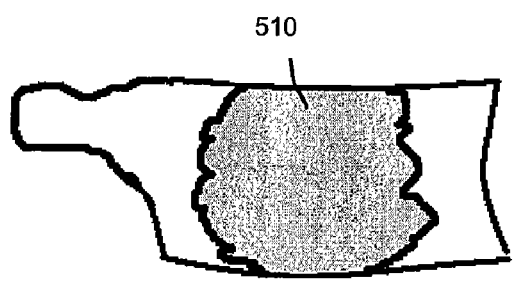
FIG. 13 is a simplified cross-sectional view of a vertebral body having a stabilizing structure in accordance with principles of the present invention.

In yet another embodiment depicted in FIG. 13, a clinician may create a relatively large cloud-like formation 510 within the vertebral body in manner similar to conventional vertebroplasty. Unlike conventional vertebroplasty, however, where a cloud of curable material is delivered to a region in the vertebral body, in this embodiment the cloud-like formation 510 is delivered to a relatively broader area within the vertebral body. The formation engages the endplates over a broad area to distribute force more evenly and prevent pressure points on the endplates. Also, the formation can extend between the endplates to provide additional stiffness.

Figure 14:
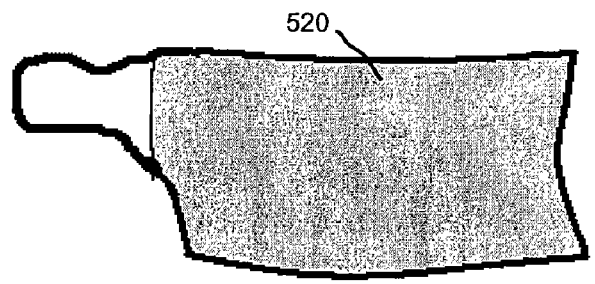
FIG. 14 is a simplified cross-sectional view of a vertebral body having a stabilizing structure in accordance with principles of the present invention.

In yet another embodiment depicted in FIG. 14, a clinician may fill substantially the entire interior of the vertebral body with curable material 520. In this embodiment the curable material 520 engages the endplates over a broad area to distribute force more evenly and prevent pressure points on the endplates. Also, the curable material 520 extends between the endplates to provide additional stiffness.

Figure 15:
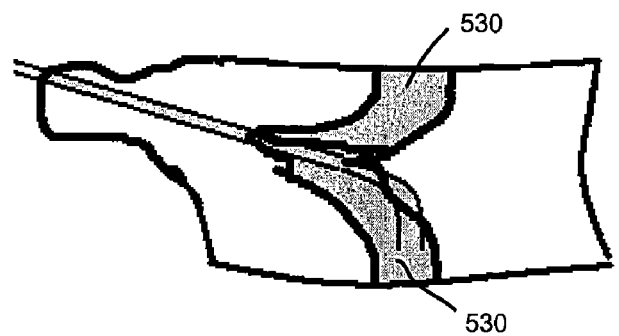
FIG. 15 is a simplified cross-sectional view of a vertebral body having a stabilizing structure in accordance with principles of the present invention.

In another embodiment depicted in FIG. 15, a curable material structure can be placed between the endplates of the vertebral body by first creating channels 530 using a curved and/or straight delivery cannula between the endplates and then filling the channels with cement. The curable material structure provides additional stiffness to the vertebral body.

Figure 16:
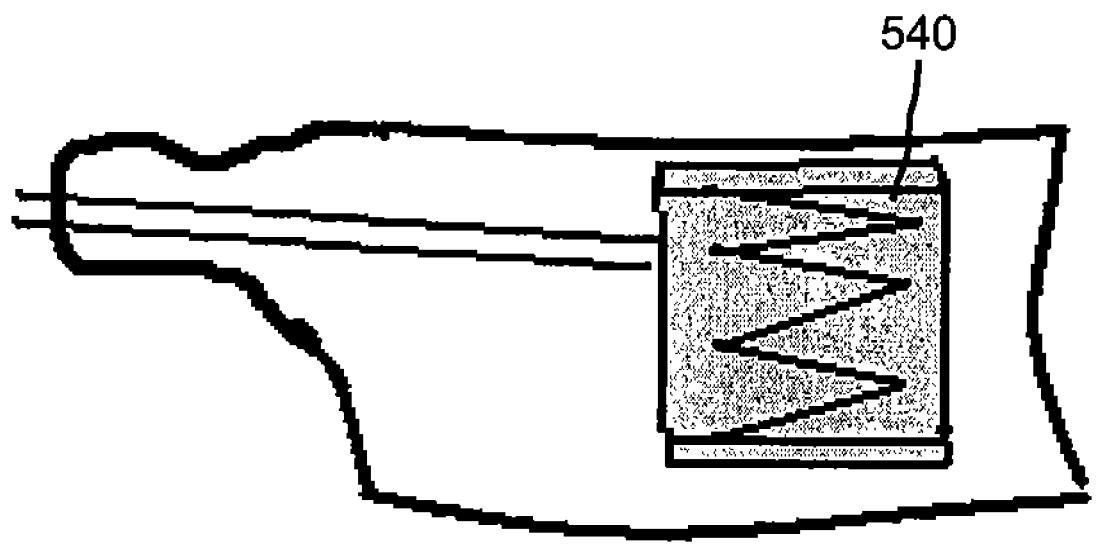
FIG. 16 is a simplified cross-sectional view of a vertebral body having a stabilizing structure in accordance with principles of the present invention.

In another embodiment, a jack-like device 540 may be used to stabilize a vertebral body. In this embodiment, as shown in FIG. 16, a collapsed expandable device is inserted into the vertebral body. According to one embodiment, the expandable device has two substantially planar supports for engaging opposite endplates of a vertebral body. In this embodiment, the planar supports are mechanically urged away from each other to expand the jack-like device 540 causing the soft body material proximal to the device to be crushed. In one embodiment, the jack-like device 540 is collapsed and removed from the vertebral body. The resulting void is then filled with curable material or another stabilizing structure. In another embodiment, the jack-like device 540 is left in the vertebral body. In this embodiment, the jack-like device 540 is positioned within the vertebral body so that upon deployment, the substantially planar supports of the device engage and support the endplates of the vertebral body. In yet another embodiment, the jack-type 540 device is left in the vertebral body and curable material is filled between the planar support and around the jack-like device. The subsequent curable material delivery further strengthens and stiffens the structure within the vertebral body. One skilled in the art will appreciate that the jack-like device 540 may also be used to restore height to the vertebral body.

In one embodiment, the jack-like 540 device may be used to directly support one or more endplates of the vertebral body. In another embodiment, the jack-like 540 device may also be used in conjunction with one or more curable material deposits proximal to an endplate of the vertebral body to stabilize the endplate. In that embodiment, the device provides a structure between the curable material deposits or between an endplate and a curable material deposit to further stabilize the vertebral body.

Figure 17:
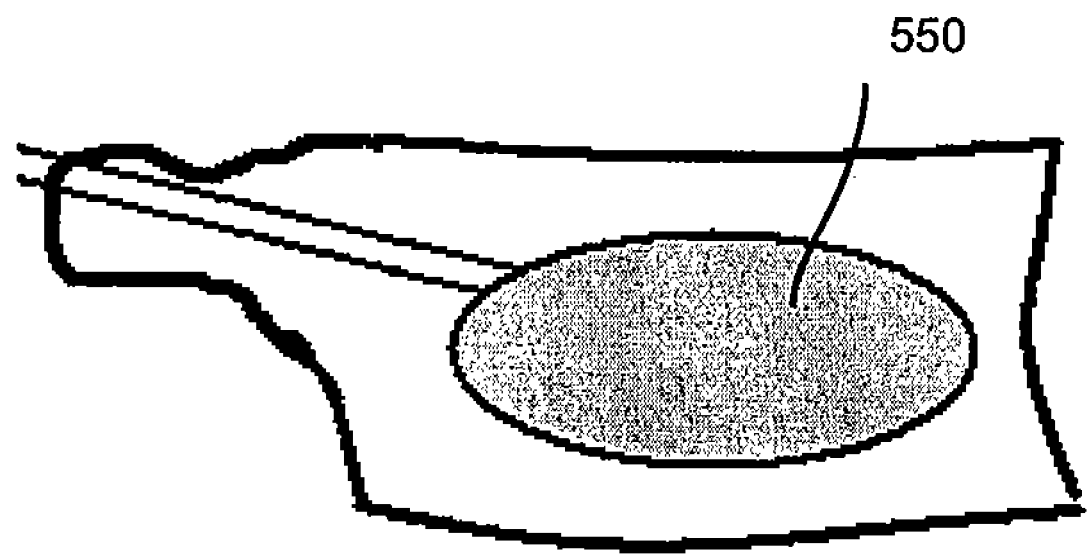
FIG. 17 is a simplified cross-sectional view of a vertebral body having an inflatable structure in accordance with principles of the present invention.

In another embodiment, an expandable container 550 may be used to stabilize a vertebral body. In this embodiment, as shown in FIG. 17, an expandable container 550 is inserted into the vertebral body and inflated, causing the soft body material proximal to the expandable container 550 to be crushed. In one embodiment, the expandable container 550 is deflated and removed from the vertebral body. The resulting void is then filled with curable material. In another embodiment, the expandable container 550 is inflated with curable material. In this embodiment, the steps of creating a void and delivering curable material can be performed at the same time.

The cement filled expandable container 550 may be used to directly support one or more endplates of the vertebral body. The balloon device may also be used in conjunction with one or more curable material deposits proximal to an endplate of the vertebral body to stabilize the endplate. In this embodiment, the cement-filled balloon provides a structure between the curable material deposits or between an endplate and a curable material deposit to further stabilize the vertebral body.

Figure 18:
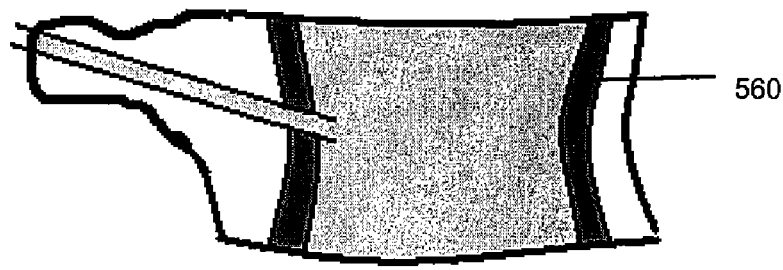
FIG. 18 is a simplified cross-sectional view of a vertebral body having a stabilizing structure in accordance with principles of the present invention.

In another embodiment, a device for bounding the flow of cement may be used to stabilize a vertebral body. As shown in FIG. 18, a boundary device 560 is inserted into the vertebral body. The device 560 can have the shape of a hollow cylinder; however, other shapes may also be used, such as a hollow cube. The boundary device 560 can be collapsible such that it can be inserted through a guide cannula. In this embodiment, the boundary device 560 has a shape memory characteristic to allow it to return to a predetermined shape after insertion into the vertebral body. In one embodiment, a void is first created in the vertebral body in the region where the boundary device 560 will be positioned. In another embodiment, the boundary device 560 may create a void within the vertebral body upon expansion. In yet another embodiment, the boundary device 560 can be placed in the vertebral body by removing the side of the vertebral body to gain access to the interior of the vertebral body.

The boundary device 560 may extend between endplates of the vertebral body and, in one embodiment, may engage the endplates of the vertebral body. Once deployed, a void is located at the interior of the boundary device 560. A delivery cannula may then be used to penetrate or otherwise access the interior void of the boundary device 560 and fill the void with curable material. In the embodiment where the boundary device 560 engages the endplates of the vertebral body, curable material is restricted from flowing outside of the void defined by the boundary device 560. Thus, curable material is maintained within a desired region within the vertebral body.

Figure 19:
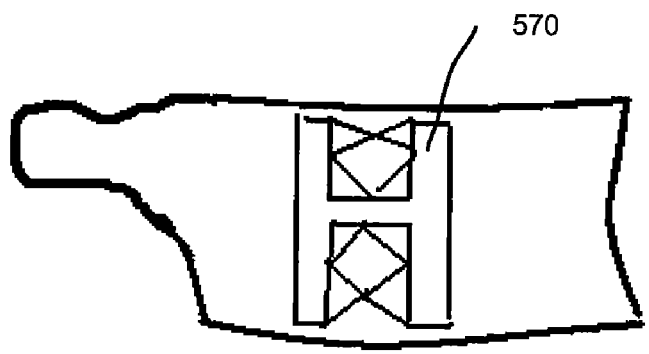
FIG. 19 is a simplified cross-sectional view of a vertebral body having a stabilizing structure in accordance with principles of the present invention.

In another embodiment, a mechanical structure may be inserted within the vertebral body to stabilize the vertebral body. In one embodiment, shown in FIG. 19, a scaffolding type structure 570 is located inside of the vertebral body to stabilize the vertebral body. In one embodiment, the scaffolding type structure 570 may be collapsible for insertion through the guide cannula and then expanded within the vertebral body after insertion. In another embodiment, the scaffolding type structure 570 may be assembled within the vertebral body. In yet another embodiment, the scaffolding type structure 570 may be placed in the vertebral body by removing the side of the vertebral body to gain access to the interior of the vertebral body.

The scaffolding type structure 570 may be used to directly support one or more endplates of the vertebral body. The scaffolding type structure 570 may also be used in conjunction with one or more curable material deposits proximal to an endplate of the vertebral body to stabilize the endplate. In this embodiment, the scaffolding type structure 570 provides a structure between the curable material deposits or between an endplate and a curable material deposit to further stabilize the vertebral body.

Figure 20:
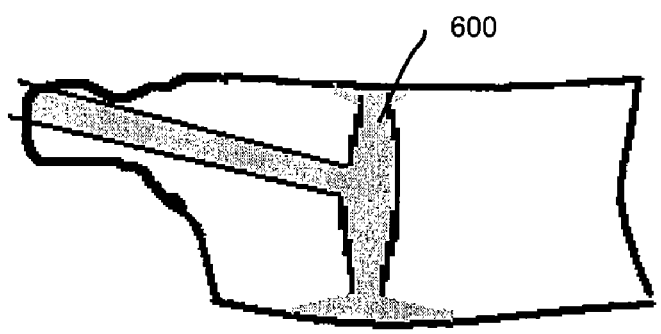
FIG. 20 is a simplified cross-sectional view of a vertebral body having a stabilizing structure in accordance with principles of the present invention.

With reference to FIG. 20, an embodiment of an apparatus and method of stabilizing the endplates of a vertebral body is shown. In one embodiment, a delivery cannula can comprise a bidirectional distal end 600 that distributes curable material in opposite directions and proximal to the endplates of the vertebral body. In the embodiment shown in FIG. 20, curable material can be distributed to top and bottom endplates at the same time. In one embodiment the distal end may comprise one or more telescoping tips to deliver curable material. In this embodiment, a collapsed telescoping distal end 600 of the delivery cannula is inserted into the vertebral body through a guide cannula. After insertion, the telescoping distal end expands to deliver material proximal to an endplate.

Figure 21:
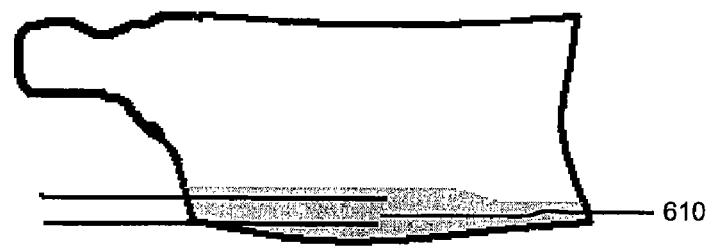
FIG. 21 is a simplified cross-sectional view of a vertebral body having a stabilizing structure in accordance with principles of the present invention.

In another embodiment, a use of a traditional straight delivery cannula may be used to deliver curable material proximal to an endplate of a vertebral body through an additional access point in the vertebral body. As shown in FIG. 21, the straight cannula 610 is placed extrapedicular to get closer to the endplates. In one embodiment, curable material may be first delivered to a first region proximal to the endplate. The delivery cannula may then be partially withdrawn from the vertebral body to deliver curable material to a second region proximal to the endplate.

Figure 22:
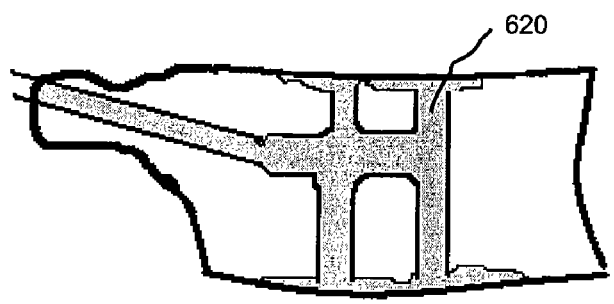
FIG. 22 is a simplified cross-sectional view of a vertebral body having a stabilizing structure in accordance with principles of the present invention.

In another embodiment, open ended bags of various shapes may be used to deliver curable material proximal to an endplate of a vertebral body to stabilize the endplate of the vertebral body. In an embodiment of FIG. 22, a preformed "H" shaped open ended bag 620 is shown. In this embodiment, a deflated bag 620 is inserted into the vertebral body and positioned to deliver curable material to the endplates of the vertebral body. Curable material is flowed into the bag 620. The preformed shape of the bag 620 guides flow of curable material so that the curable material is delivered proximal to the top endplate and bottom endplate of the vertebral body. In the embodiment shown in FIG. 22, the "H" shaped bag allows curable material to be delivered proximal to the endplates through multiple channels. Although an "H" shaped bag 620 is shown in FIG. 22, other shaped bags may be used such as "I" shaped bags, generally spool or cylindrical shaped bags or spoke-like shaped bags.

In one embodiment, the open ended bag is left within the vertebral body substantially filled with curable material. After hardening, a rigid structure is formed between the endplates to further stiffen and stabilize the vertebral body. In another embodiment, the bag may be removed and curable material is delivered into the voids created by the bag.

Figure 23:
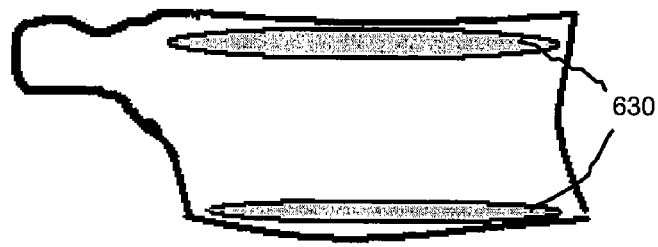
FIG. 23 is a simplified cross-sectional view of a vertebral body having a stabilizing structure in accordance with principles of the present invention.

In another embodiment, one or more bags may be placed proximal to the endplates of the vertebral body to stabilize the endplates of the vertebral body. In one embodiment shown in FIG. 23, a disk shaped bag 630 is placed proximal to each endplate for supporting the endplate. Curable material may then be delivered between the bags 630 to connect the bags forming a rigid structure to stiffen and stabilize the vertebral body. Other structures as disclosed herein may also be used to connect the bags 630 to form a stabilizing structure.

Figure 24:
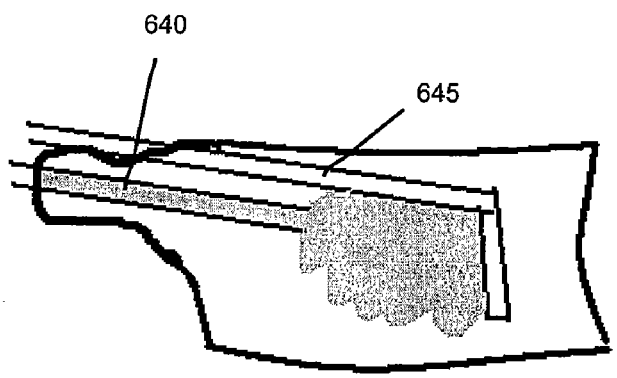
FIG. 24 is a simplified cross-sectional view of a vertebral body having a stabilizing structure in accordance with principles of the present invention.

In another embodiment, two cannulas can be used to aid in delivering curable material to specific desired regions within a vertebral body to stabilize the vertebral body. With reference to FIG. 24, in one embodiment, a first delivery cannula 640 is used to deliver curable material to a region within a vertebral body. A second delivery cannula 645 is inserted into the vertebral body to act as a boundary to prohibit the flow of curable material into undesired regions within the vertebral body. As shown in the embodiment of FIG. 24, the second delivery cannula 645 can be curved to more effectively prohibit the migration of curable material into an undesired location.

Figure 25:
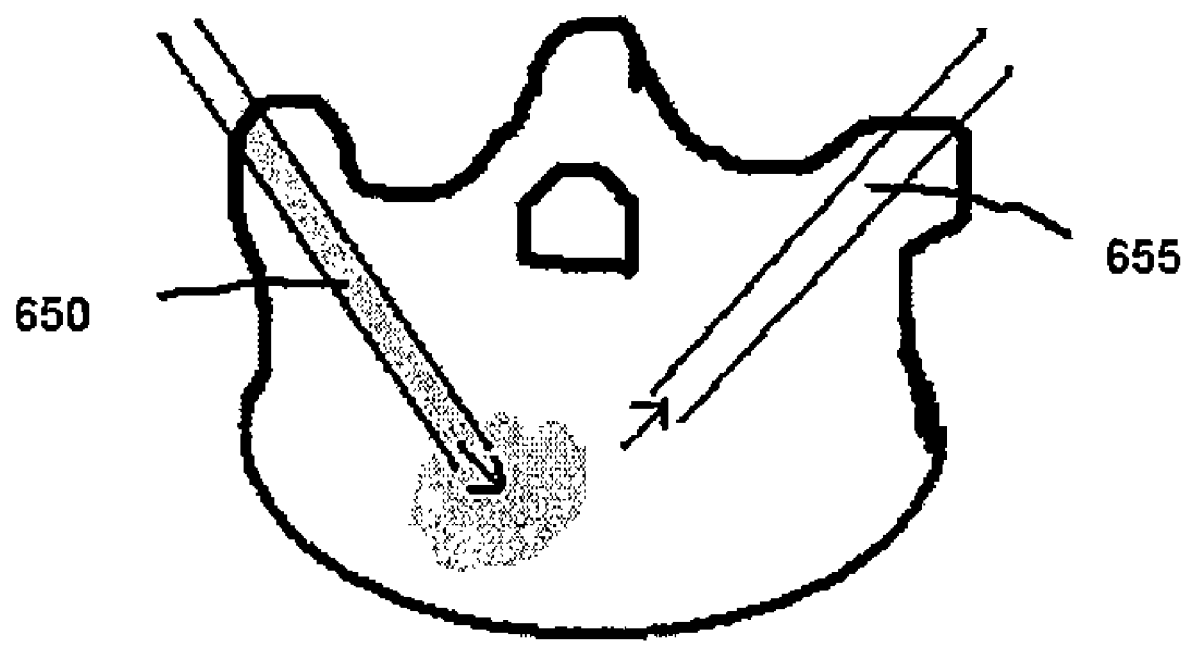
FIG. 25 is a simplified cross-sectional view of a vertebral body, illustrating the delivery of curable material in accordance with principles of the present invention.

In another embodiment a delivery cannula can be used in conjunction with a vacuum cannula connected with a vacuum source to deliver cement to specific desired regions within a vertebral body to stabilize the vertebral body. With reference to FIG. 25, a delivery cannula 650 delivers curable material to the interior of the vertebral body. A vacuum cannula 655 is also employed to remove soft body material and excess cement. In this embodiment, the removal of the soft body material by vacuum creates a void that aids in directing the flow of cement. The vacuum within the vertebral body also aides in pulling cement from the delivery cannula 650, thus assisting in delivering curable material to the vertebral body. In one embodiment, a container or bag may be placed in the void that is created by the vacuum prior to delivery of curable material.

In another embodiment curable material may be proximal to an endplate through the use of a magnetic contrast agent and a magnetic field. In this embodiment, magnetic contrast agent may be added to the curable material and the curable material is injected into the vertebral body. A magnetic field may then be applied to the vertebral body to move the magnetic curable material to a desired location, such as an endplate.

Void Creation

Figure 26A:
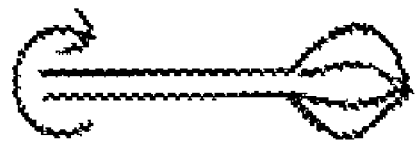
FIGS. 26A-F are simplified perspective views of a distal portion of the delivery cannula in accordance with principles of the present invention.
Figure 26B:
Figure 26C:
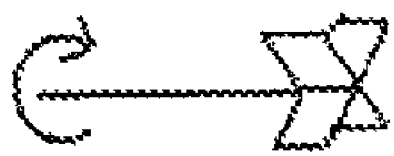
Figure 26D:
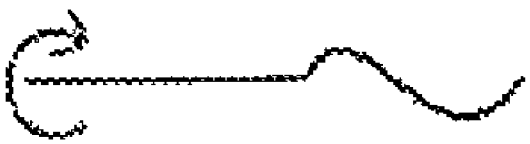
Figure 26E:
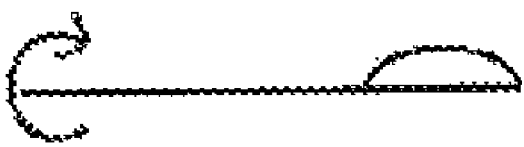
Figure 26F:

While the creation of voids within the vertebral body has been described with reference to a curved delivery cannula, other methods and structures may also be used to create voids within a vertebral body or stabilize the endplates of a vertebral body. With regard to the creation of voids, the distal end 82 of the delivery cannula 36 may take several various forms. With reference to FIGS. 26A-26F, configurations are shown that may be used to create voids within the vertebral body, macerate the soft tissue within the vertebral body, remove tissue from the vertebral body and/or deliver curable material to the vertebral body. FIG. 26A discloses a generally whisk shaped distal end. FIG. 26B discloses a generally coil ball shaped distal end. FIG. 26C discloses a generally "wind mill" shaped distal end. FIG. 26D discloses a generally waved shaped distal end. FIG. 26E discloses a generally half moon shaped distal end. FIG. 26F discloses a generally L shaped distal end. The above embodiments may be operable to collapse within the guide cannula during insertion into the vertebral body and possess a shape memory characteristic to revert back to the preformed shapes once inserted into the vertebral body. The above distal tip embodiments may also be left inside the vertebral body after voids have been created and curable material has been delivered to the vertebral body. Where the distal end configurations are used to deliver curable material to the vertebral body, one or more orifices may be located on the distal end to expel curable material in a variety of desired directions.

Figure 27A:
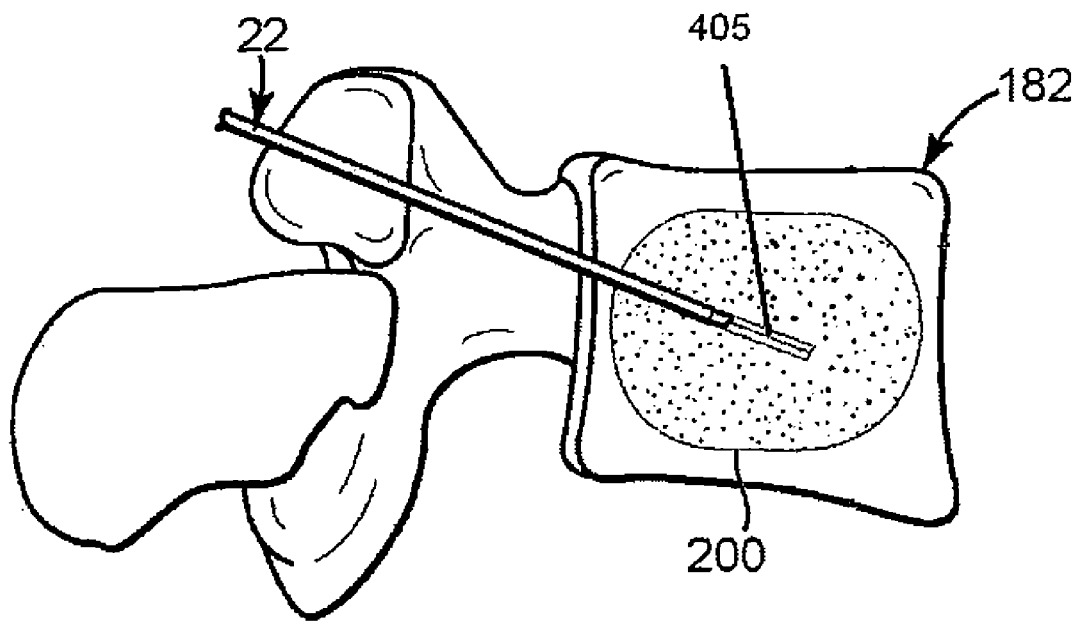
FIGS. 27A and 27B are partial cross-sectional views of a vertebral body, illustrating use of the system in accordance with principles of the present invention.
Figure 27B:
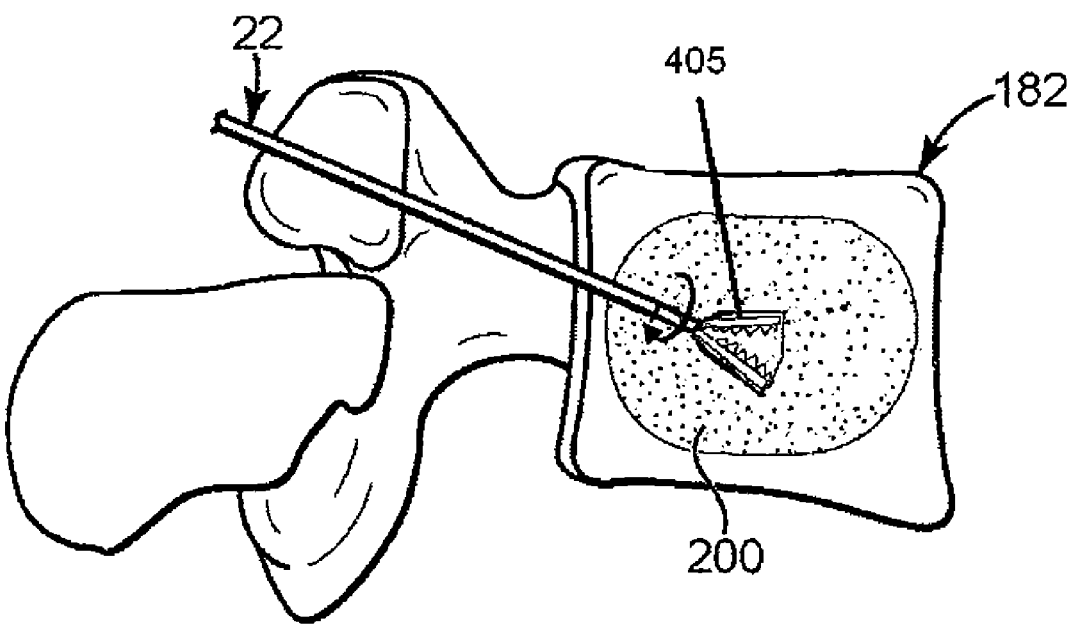

With reference to FIGS. 27A-B, in another embodiment of a device for creating voids within a vertebral body, mechanical jaws may be used to create a void. In this embodiment, single or dual hinged jaws 405 can be inserted in a closed position through the access cannula 22 and into the vertebral body. Once inserted inside of the vertebral body, the clinician can expand the metal jaws and rotate the jaws 405 to create a void.

Figure 28A:
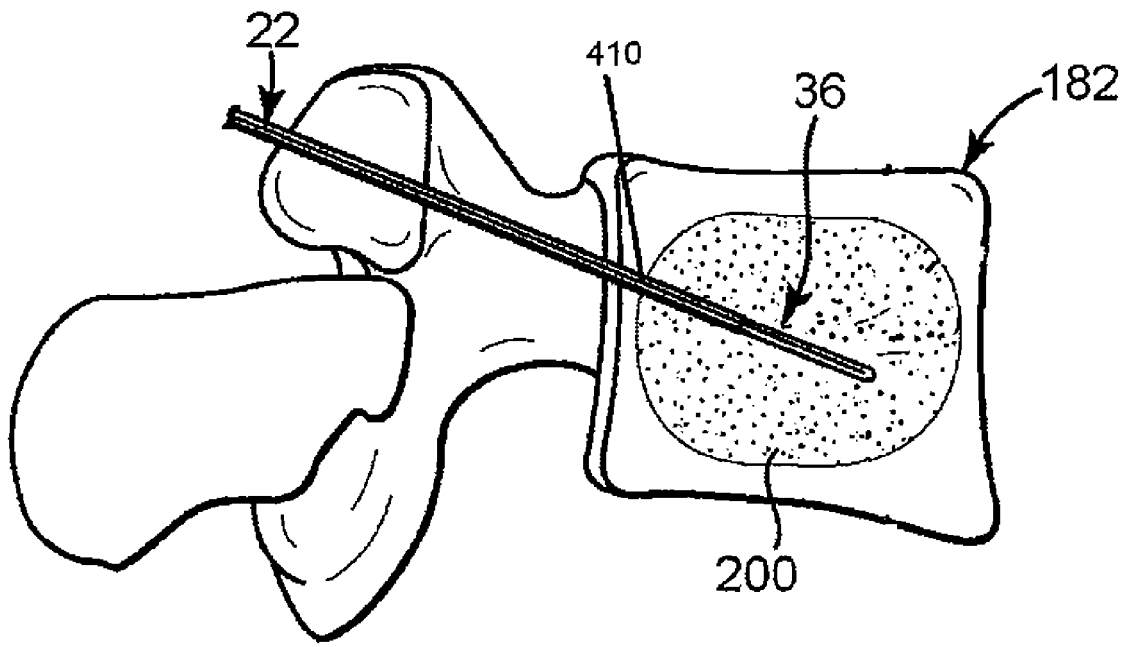
FIGS. 28A and 28B are partial cross-sectional views of a vertebral body, illustrating use of the system in accordance with principles of the present invention.
Figure 28B:
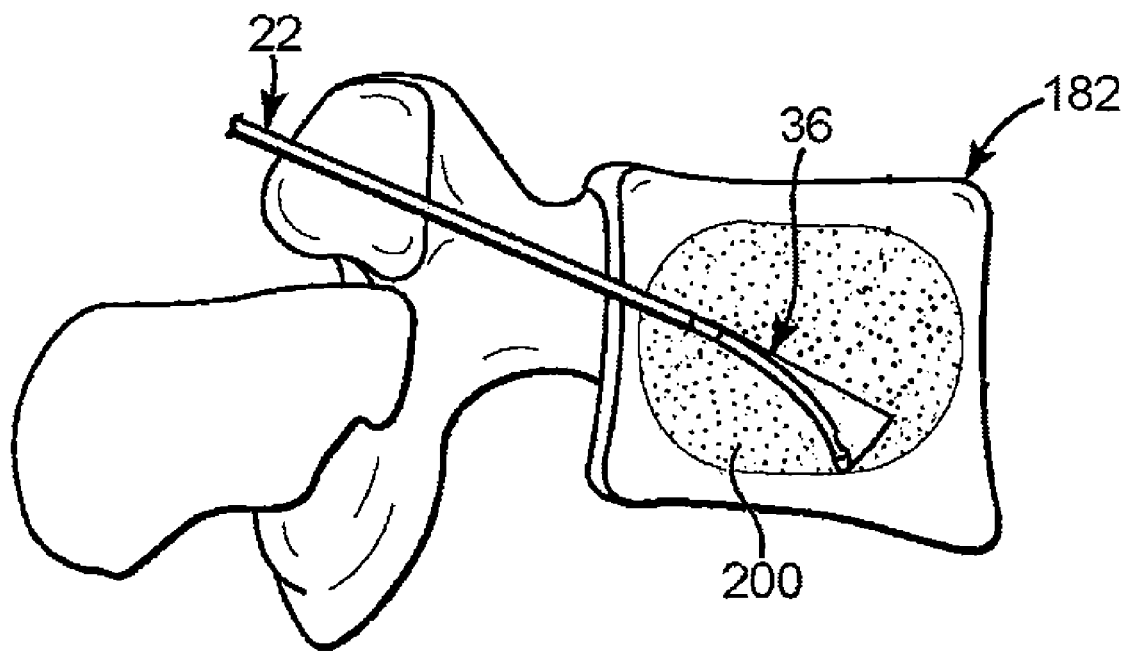

With reference to FIG. 28A-B, in another embodiment, a straight wire 410 can be inserted into the deflectable segment of the delivery cannula 36 to straighten the deflectable segment. The straight wire 410 and delivery cannula 36 are inserted into the vertebral body. A clinician then removes the straight wire 410 from the delivery cannula, allowing the deflectable segment to revert back to a curved shape, thus creating a void.

Figure 29A:
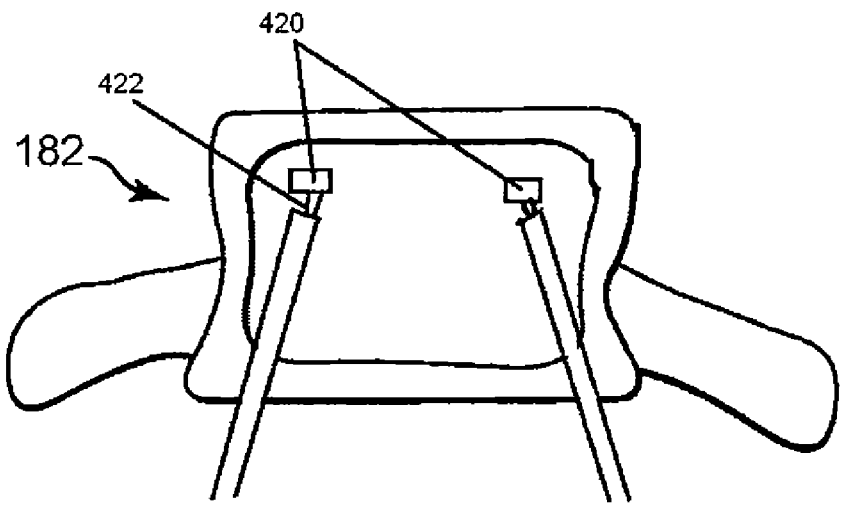
FIGS. 29A, 29B and 29C are partial cross-sectional views of a vertebral body, illustrating use of the system in accordance with principles of the present invention.
Figure 29B:
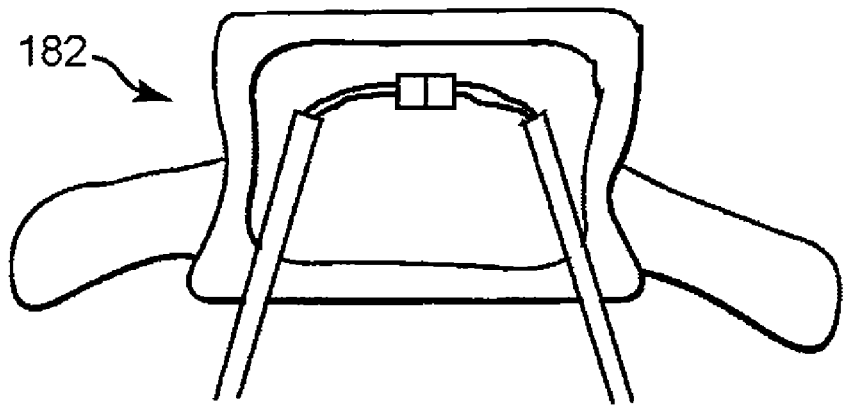
Figure 29C:
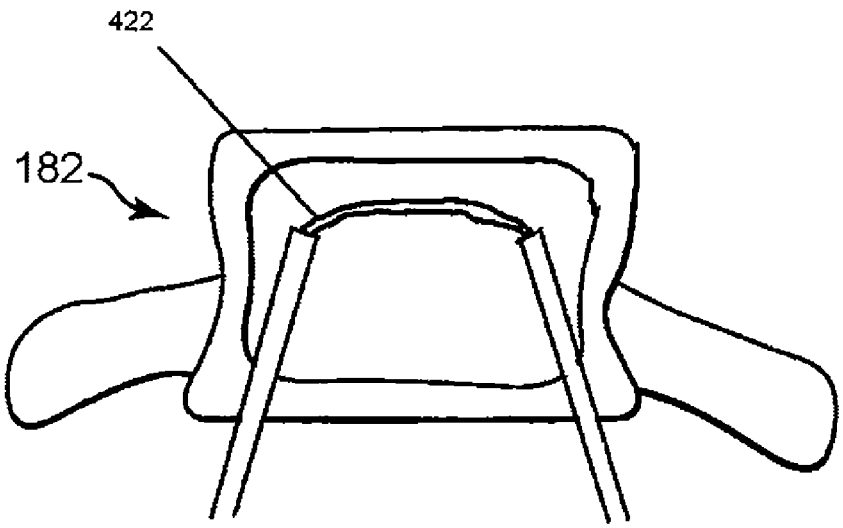

With reference to FIG. 29A-29C, in another embodiment, one or more magnets 420 and a wire 422 may be used to create a void within the vertebral body. In this embodiment, a clinician takes a bi-pedicular approach into the vertebral body and preferably positions the access cannulas proximal to an end plate. In one embodiment, two magnets 420, each attached to a wire 422, are inserted into the vertebral body through the access cannulas. The magnets are attracted to each other and move toward each other until contact is made. The clinician then pulls one of the wires 422 to pull the two magnets 420 out of one of the access cannulas, leaving a single wire within the vertebral body. The clinician can then pull the cannulas and wire 422 to sever the cancelous bone in its path and create a void proximal to an endplate. The void may be filled with curable material through the access cannula, or a delivery cannula may also be used. Multiple void creation procedures may be employed to create several planes of voids within the vertebral body.

Figure 30:
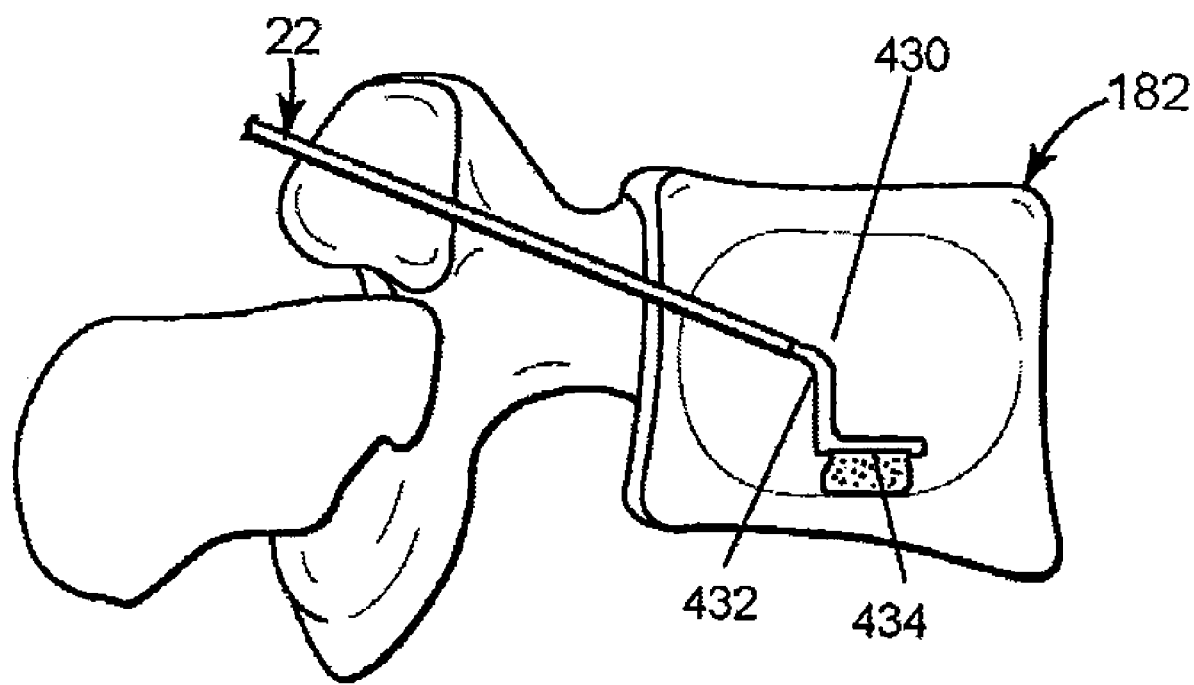
FIG. 30 is a simplified cross-sectional view of a vertebral body showing the delivery of curable material in accordance with principles of the present invention.

With reference to FIG. 30, an elongated deflectable segment 430 is shown. In this embodiment, the elongated deflectable segment 430 forms a relatively shallow curve 432 with an elongated slot 434. The clinician can create elongated shallow voids with the elongated deflectable segment 430 and inject discrete lines of curable material proximal to an endplate. Alternatively, a clinician can inject a large bolus of cement into the region and spread the bolus in the desired area with the elongated deflectable segment 430.

Figure 31A:
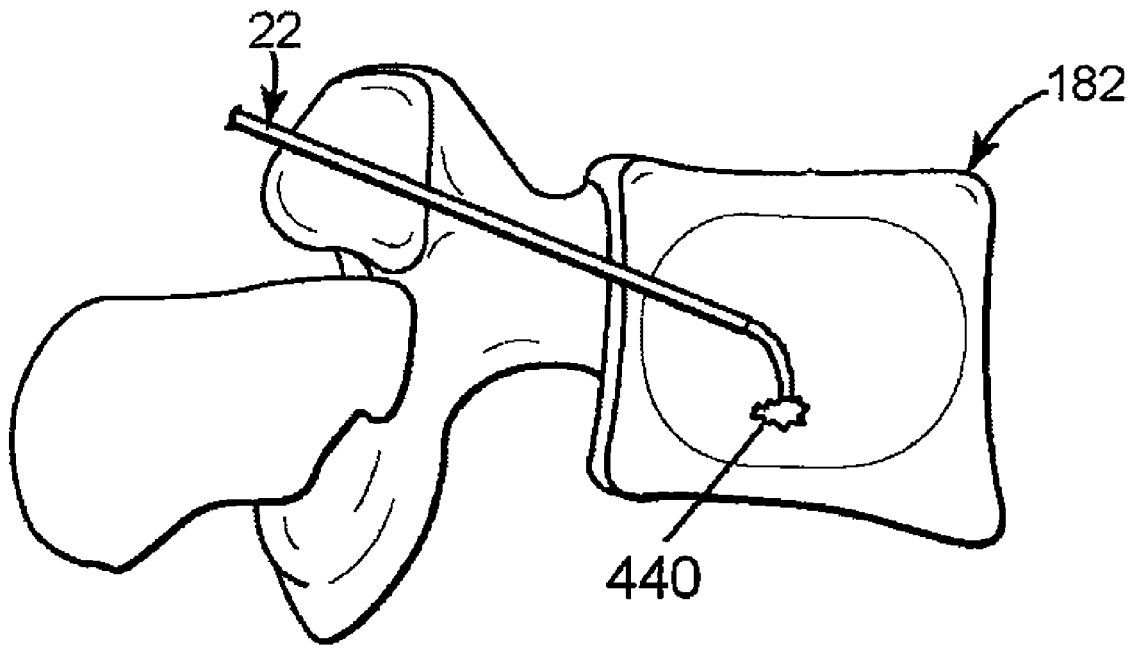
FIGS. 31A and 31B are simplified cross-sectional views of a vertebral body showing the delivery of curable material in accordance with principles of the present invention.
Figure 31B:
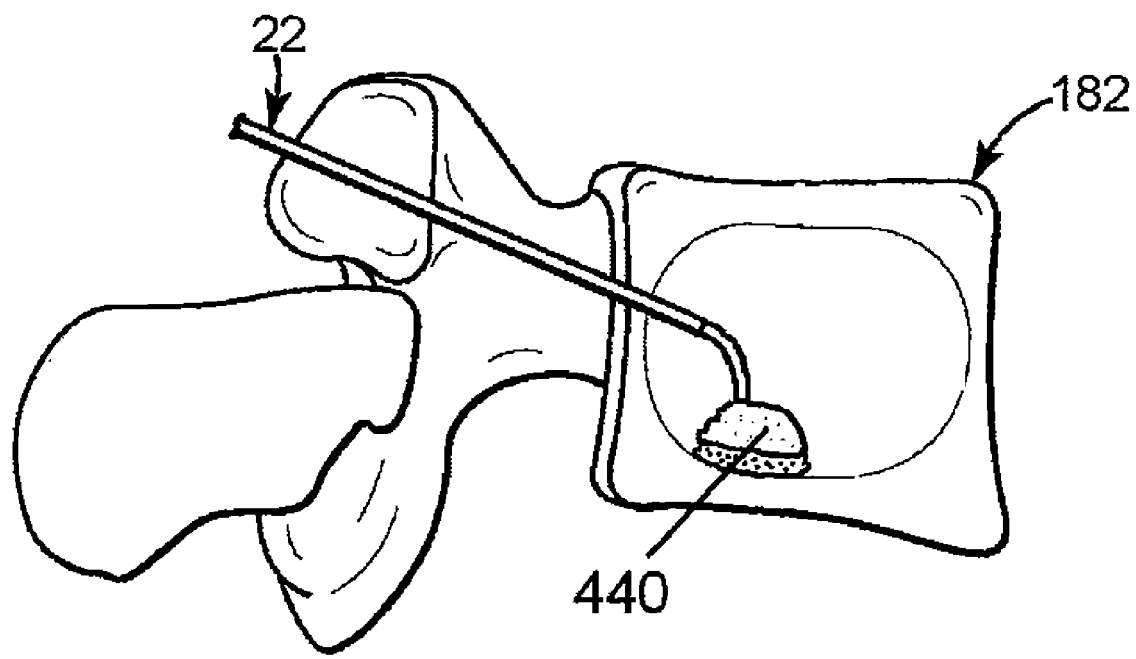

With reference to FIG. 31A-31B, another embodiment for creating a void and injecting curable material is disclosed. In this embodiment, a porous expandable container 440 is shown. The porous expandable container 440 is inserted into a vertebral body through a curved delivery cannula such that the porous expandable container 440 is located proximal to an endplate. Curable material is then injected into the porous expandable container 440. As curable material fills and expands the porous expandable container 440, the porous expandable container 440 creates a void within the vertebral body. Also, as curable material fills and expands the porous expandable container 440, the pores on the porous expandable container 440 become larger, allowing the curable material to be distributed proximal to the endplates. After the curable material is distributed, the porous expandable container 440 may be removed from the vertebral body, or may be left in.

Figure 32A:
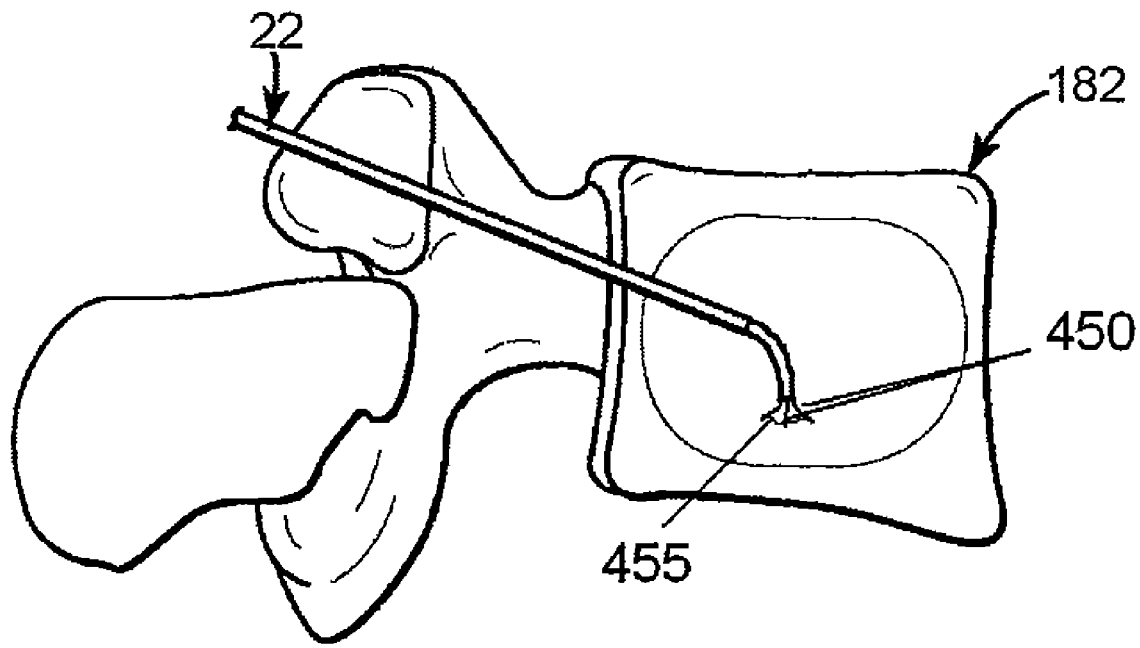
FIGS. 32A and 32B are simplified cross-sectional views of a vertebral body showing the delivery of curable material in accordance with principles of the present invention.
Figure 32B:
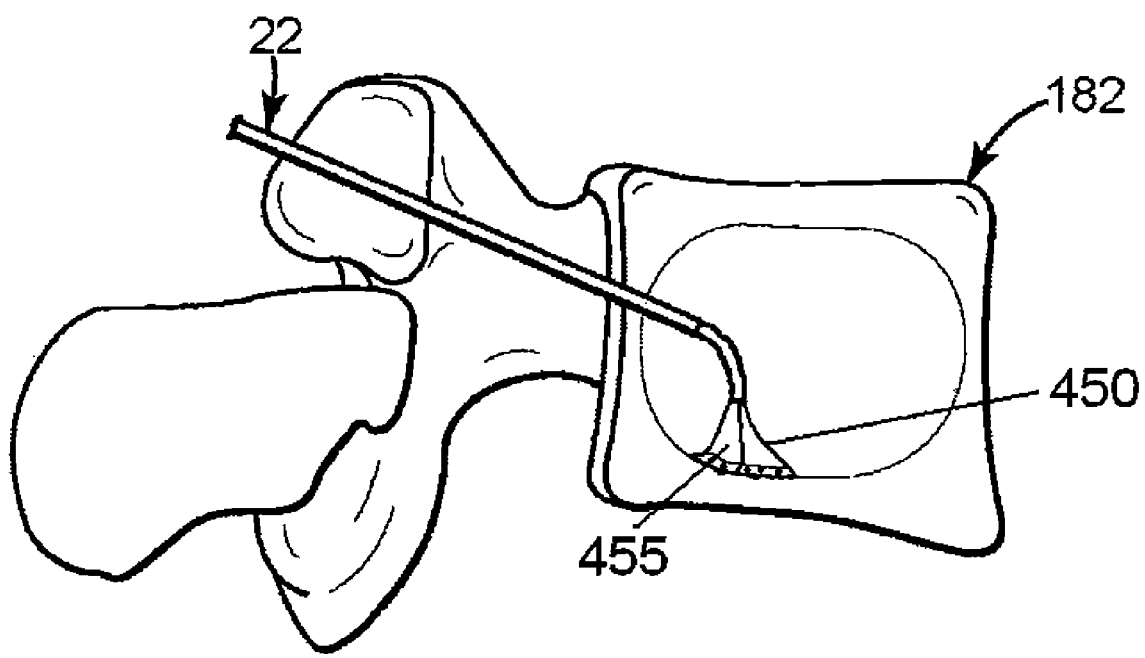

With reference to FIG. 32A-32B, another embodiment for creating a void and injecting curable material is disclosed. In this embodiment, a plurality of curved wires 450 having a shape memory characteristic is surrounded by an expandable sheath 455. As the curved wires are inserted into the vertebral body, they revert back to a curved shape. The curved wires 450 are oriented generally to curve in opposite directions. The curved wires 450 are surrounded by a sheath 455 that may expand as the curved wires 450 revert to their curved shape. In this way, the wire 450 and sheath 455 create a void within the vertebral body. Curable material may then be injected into the interior of the sheath 455 and into the void. After the curable material is distributed, the curved wires 450 and sheath 455 may be removed from the vertebral body.

In another embodiment of a device and method for creating a void in a vertebral body, a clinician may use an articulated wire that allows a clinician to steer an end of the articulated wire to a desired location within the vertebral body. The steerable articulated wire may allow a clinician to more precisely create voids of desired location, shape and size within the vertebral body. Further, the steerable articulated wire may be reusable for different procedures.

In another embodiment of a device and method for creating a void in a vertebral body, a plurality of overlapping hinged segments connected with an end of a delivery cannula may also be used. In this embodiment, the overlapping hinged segments are collapsed when inserted into the vertebral body and placed proximal to a desired location, such as an endplate. When curable material is injected though the delivery cannula, the overlapping hinged segments hinge outward and expand, thus creating a void. Curable material may then be delivered into and proximal to the void.

In another embodiment of an apparatus and method for creating a void in a vertebral body, a group of tangled filaments may be placed proximal to the top and bottom endplates of a vertebral body. In this embodiment, the tangled filaments create a void in the vertebral body proximal to the endplates during positioning of the tangled filaments. Curable material is then injected into the tangled filaments and, thus, into the void created by the tangled filaments. The tangled filaments may also act to confine the curable material to the desired injection area and act to strengthen the structure by forming a filament reinforced curable material structure.

According to another embodiment, voids may be created within the soft tissue of the vertebral body through the use of electrical, chemical or thermal means. In one embodiment, a probe emitting high intensity radio frequencies can be inserted into the vertebral body. The radio frequencies can destroy soft body material and create voids within the vertebral body. According to another embodiment, voids can be created though ablation. In this embodiment, an electrically charged probe can be inserted into the vertebral body. The probe generates high temperatures within the vertebral body to destroy soft body material and create voids. Other methods for exposing soft body material to high temperatures may be used as well. In another embodiment, soft body material may be frozen when exposed to a super-cooled probe or liquid nitrogen. Freezing of the soft body material destroys soft body material and creates voids within the vertebral body.

Height Restoration

In other embodiments of the present invention, height restoration of the vertebral body is achieved prior to stabilizing the vertebral body. In one embodiment, height restoration can be achieved through the use of devices within the vertebral body. In one example discussed above, a generally cylindrical mesh bag having ends that engage the endplates of a vertebral body can restore height to a vertebral body as the mesh bag is inflated.

Figure 33A:
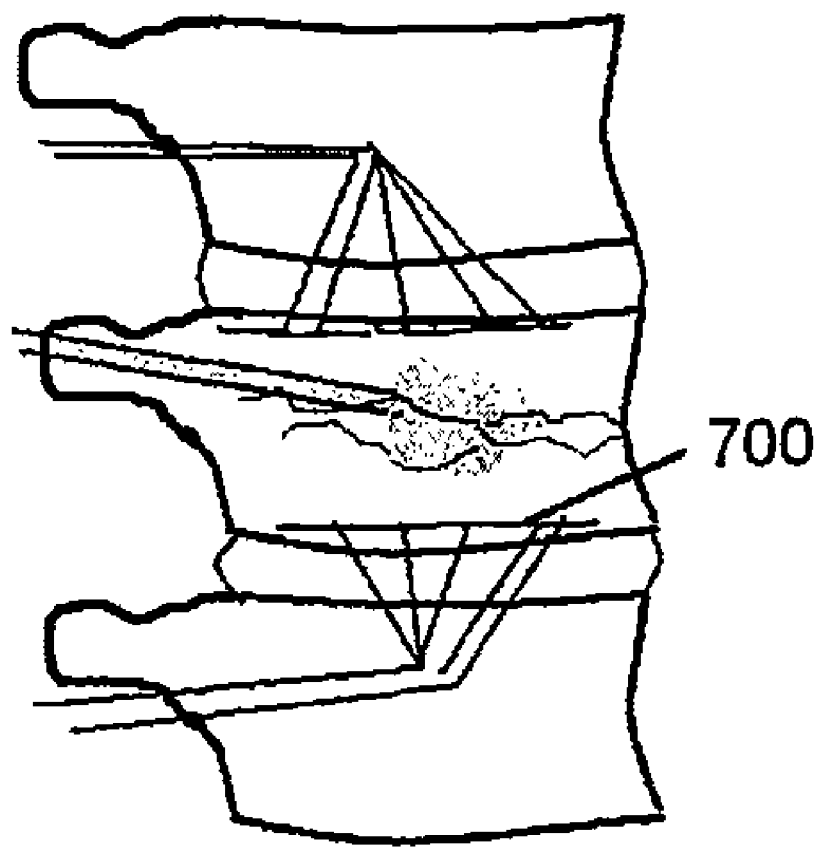
FIGS. 33A and 33B are simplified cross-sectional views of a vertebral body showing the restoration of vertebral body height in accordance with principles of the present invention.

In another embodiment, height can be stored by accessing one or both endplates of the damaged vertebral bodies through an adjacent vertebral body and pulling the one or more endplates to restore the vertebral body's pre-fractured height. In the embodiment shown in FIG. 33A, the vertebral body in the center is fractured. In this embodiment, a clinician first accesses the vertebral bodies adjacent to the damaged vertebral body. One or more access points are then created through the intervertebral disks and into the damaged vertebral body. Fasteners 700 operable to engage the inside surfaces of the endplates are placed through the one or more access points. The fasteners 700 are then pulled in opposite directions to restore the vertebral body to its undamaged height. Curable material may then be delivered to the vertebral body. In one embodiment, the fasteners 700 can be hinged rods on cables that allow the rods to be placed through an access point, but then swing to engage the inner surface of the endplate once inserted into the vertebral body. Other fasteners 700 such as hooks may also be used.

Figure 33B:
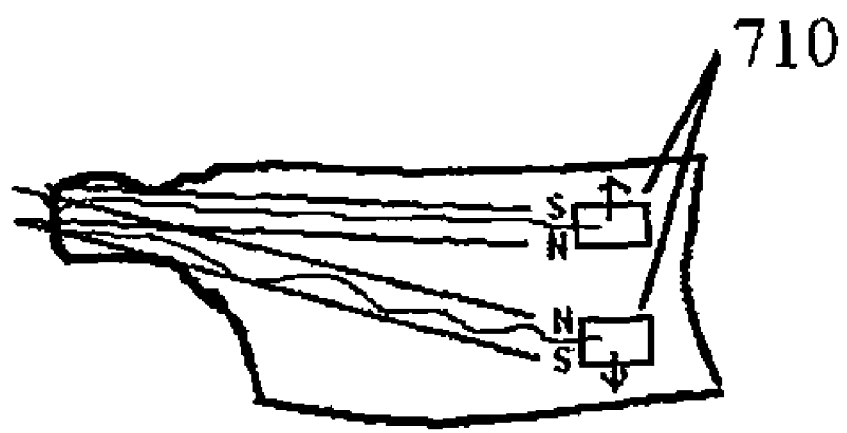

In another embodiment, magnets may be used to restore height to a damaged vertebral body. In the embodiment depicted in FIG. 33B, two electromagnets 710 are inserted into the vertebral body and placed next to each other near the fractured side of the vertebral body. The magnets 710 are oriented so that the poles of the magnets are opposite one another. When the magnets 710 are activated the magnets 710 are repelled from each other, causing the endplates to move in opposite directions. A clinician can continue to move the magnets 710 until the vertebral body achieves its pre-fractured height. In one embodiment, the magnets can be left in the vertebral body. In another embodiment curable material is then delivered to the vertebral body to stabilize the vertebral body at its restored height.

In another embodiment, height restoration can be achieved by positioning the patient's body to cause flexing of the spine to restore the height of a damaged vertebral body to its pre-fractured height. An external support structure is placed under the patient's body to position the body to achieve height restoration of a damaged vertebra. It has been observed that by using an external support structure placed in the correct position, significant restoration of height and correction of kyphosis can be achieved. Thus external support structures can be designed to facilitate postural reduction of collapsed vertebral bodies. The external support structures can be used pre-operatively, during the operation and post-operatively to facilitate postural reduction of collapsed vertebral bodies.

In an embodiment where a patient is placed in a supine position, an external support structure placed proximal to the fractured vertebral body flexes the spine in a manner to cause the endplates of the fractured vertebral body to be urged away from each other thereby restoring height in the fractured vertebral body. By monitoring the fractured vertebral body under fluoroscopic imaging, the clinician can position the external support structure to achieve the desired height restoration. The external support structure should be made of a material that does not interfere with the imaging. In some cases, the external support structure promotes better imaging because the patient is lifted off, of the stainless steel operating table.

In another embodiment where a patient is placed in a prone position, two external support structures may be placed distal from the fractured vertebral body. The external support structures flex the spine in a manner to cause the endplates of the fractured vertebral body to be urged away from each other, thereby restoring the height in the fractured vertebral body. By monitoring the fractured vertebral body under fluoroscopic imaging, the clinician can position the pillow to achieve desired height restoration. In one preferred embodiment, the external support structures are generally half-cylindrically shaped. Other shapes may also be used.

In one embodiment, the external support structure is a softened structure such as a pillow. It has been observed that placement of one or more pillows under a patient during surgery can have the added benefit of providing comfort to the patient who is otherwise lying on a flat and hard operating table. Increased patient comfort reduces patient movement during surgery. Less movement by the patient can make imaging and performing the procedure more efficient.

Additional methods and apparatus exist for stabilizing a vertebral body via adjacent vertebral bodies. In one embodiment, curable material can be delivered to two adjacent vertebral bodies through one access point in one of the vertebral bodies. With reference to FIGS. 34A-34B, first vertebral body and a second vertebral body are shown. An access point is created into the first vertebral body according to conventional methods. A curved, or otherwise shaped needle, is used to puncture through the upper endplate of the first vertebral body, the intervertebral disk and the lower endplate of the second vertebral body. An access point 720 is thus created to the interior of the second vertebral body. In the embodiment of FIG. 34A, a distal end of a curved delivery cannula is then inserted into the second vertebral body to deliver curable material to the second vertebral body according to one of the methods described herein. With reference to FIG. 34B the distal end of the delivery cannula is then partially withdrawn into the first vertebral body and curable material is delivered to the interior of the first vertebral body.

With reference to FIG. 34C, according to one embodiment, curable material can also be delivered between the first vertebral body and second vertebral body to connect the deposits of curable material in each vertebral body. In this embodiment the resulting curable material deposit 722 may form a generally dumbbell shape. By connecting the curable material deposits in two different vertebral bodies, the two vertebral bodies can be rigidly connected with each other.

In another embodiment, curable material can be delivered to the exterior of a fractured vertebral body. With reference to FIG. 35, a first vertebral body and a fractured second vertebral body are shown. In this embodiment, access to the exterior surface of a fractured endplate is achieved by first accessing the interior of the first vertebral body and puncturing through an endplate of the first vertebral body and the intervertebral disk. This puncture creates an access point to the exterior surface of the fractured endplate. Using a curved delivery cannula, curable material can be delivered through the access point to the exterior surface of the fractured endplate. In this embodiment, curable material can be deposited in a manner to fill the void left by the fracture. Such a deposit can effectively restore the height of the fractured vertebral body relative to the adjacent vertebral bodies even though the fractured endplate of the second vertebral body was not actually restored to a pre-fracture height. In another embodiment, access to the exterior of the damaged endplate can be achieved through the intervertebral disk without accessing an adjacent vertebral body.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof. For example, while specific reference has been made to vertebroplasty procedures, the devices, systems, and methods in accordance with principles of the present invention are equally applicable to delivering curable material within multiple other bones of a patient.

What is claimed is:

1. A method of stabilizing a vertebral body comprising the steps of:
   delivering curable material contacting a first endplate to support the first endplate; and, thereafter,
   forming a stabilizing structure within a mesh bag that includes pores permitting flow of material through the mesh bag and that is disposed between the first endplate and a second endplate to provide structural support between the first endplate and second endplate, the mesh bag configured to engage and support the curable material contacting the first endplate.

2. The method of claim 1 wherein curable material is delivered using delivery cannulas having different curvatures.

3. The method of claim 1 wherein the material within the mesh bag is bone in-growth material.

4. The method of claim 1 wherein the material within the mesh bag is curable material.

5. The method of claim 1 further comprising the step of creating voids within the vertebral body prior to delivering curable material by using mechanical jaws rotated within the vertebral body.

6. The method of claim 1 further comprising the step of creating voids within the vertebral body prior to delivering curable material by using magnets inserted into the vertebral body.

7. The method of claim 1 further comprising the step of restoring height to the vertebral body prior to delivering curable material.

8. A method of creating a stabilizing structure within a vertebral body comprising the steps of:
   accessing a vertebral body, having two endplates, with an access cannula;
   inserting a collapsible container within the vertebral body, the collapsible container comprising a mesh bag that includes pores permitting flow of material through the mesh bag;
   delivering curable material contacting a first of the two endplates to support the first endplate and delivering curable material contacting a second of the two endplates to support the second endplate; and, after the delivering step,
   inflating the collapsible container with a material such that the height of the collapsible container is at least about 80% of the height of the vertebral body between the two endplates and such that the collapsible container engages the curable material contacting each of the two endplates.

9. The method of claim 8 wherein the collapsible container is a mesh bag inflated with bone in-growth material.

10. The method of claim 8 wherein voids are created within the vertebral body at the location prior to inserting the collapsible container at the location of where the collapsible container will be inserted.

* * * * *